(12) United States Patent
Hanada et al.

(10) Patent No.: US 7,037,919 B1
(45) Date of Patent: May 2, 2006

(54) TETRAHYDROQUINOLINE DERIVATIVES

(75) Inventors: Keigo Hanada, Kyoto (JP); Kazuyuki Furuya, Kyoto (JP); Kiyoshi Inoguchi, Kyoto (JP); Motonori Miyakawa, Kyoto (JP); Naoya Nagata, Kyoto (JP)

(73) Assignee: Kaken Pharmaceutical Co. Ltd., Tokyo (JP)

( * ) Notice: Subject to any disclaimer, the term of this patent is extended or adjusted under 35 U.S.C. 154(b) by 398 days.

(21) Appl. No.: 10/110,636

(22) PCT Filed: Oct. 6, 2000

(86) PCT No.: PCT/JP00/07007

§ 371 (c)(1),
(2), (4) Date: Aug. 14, 2002

(87) PCT Pub. No.: WO01/27086

PCT Pub. Date: Apr. 19, 2001

(30) Foreign Application Priority Data

Oct. 14, 1999 (JP) .......................... 11-292021

(51) Int. Cl.
- *A61K 31/473* (2006.01)
- *A61K 31/4741* (2006.01)
- *A61K 31/4745* (2006.01)
- *C07D 221/06* (2006.01)
- *C07D 491/048* (2006.01)

(52) U.S. Cl. ............. 514/290; 514/215; 514/291; 514/292; 514/298; 546/79; 546/80; 546/81; 546/84; 546/87; 546/89; 546/93; 546/108; 540/580

(58) Field of Classification Search .............. 546/79, 546/93, 108, 81, 84, 87, 89, 80; 540/580; 514/215, 290, 291, 292, 298

See application file for complete search history.

(56) References Cited

U.S. PATENT DOCUMENTS 4,607,054 A  8/1986  Bouton et al.
5,288,725 A  2/1994  Witherup et al.
5,925,527 A  7/1999  Hayes et al.

FOREIGN PATENT DOCUMENTS

WO  WO 96/19458  8/1998
WO  WO 98/34111  8/1998

OTHER PUBLICATIONS

Edwards JP et al. Bioorganic & Medicinal Chemistry Letters 9 (1999) 1003–1008.*
Kobayashi et al., Biotechnology and Bioengineering 61: 23–31 (1998).
Batey et al., Chem. Commun. 1999, 651–652.
Snider et al., Tetrahedron Letters 40: 3339–3342 (1999).
Tectsch et al. Annais of the New York Academy of Sciences, 1995 (Jun. 12), 761: 5–24.*
Trachtenberg et al. Molecular Urology, 1998, 2(3): 201–207.*
Hammond et al. Anti–Cancer Drugs (2002, 13(8): 781–790.*

* cited by examiner

*Primary Examiner*—Evelyn Mei Huang
(74) *Attorney, Agent, or Firm*—Nixon Peabody LLP

(57) ABSTRACT

Tetrahydroquinoline derivatives of general formula (I) or salts thereof, having a specific and strong binding affinity for AR and exhibiting AR agonism or antagonism; and pharmaceutical compositions containing the derivatives or the salts.

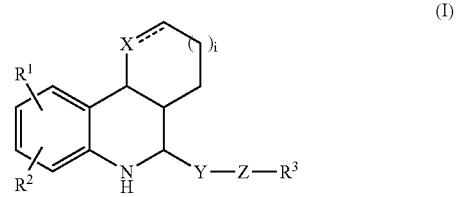

(I)

2 Claims, No Drawings

TETRAHYDROQUINOLINE DERIVATIVES

This application is the U.S. National stage of International Application No. PCT/JP00/07007 filed Oct. 6, 2000 which claims the benefit under 35 U.S.C. § 119(a) of Japanese Patent Application No. 11/292021 filed Oct. 14, 1999 with the Japanese Patent Office under the Paris Convention for the Protection of Industrial Property (613 O.G. 23, 53 Stat. 1748).

TECHNICAL FIELD

This invention relates to tetrahydroquinoline derivatives or salts thereof which have a specific and strong binding affinity for androgen receptors and exhibit androgen receptor agonism or antagonism, and pharmaceuticals containing the derivatives or the salts.

BACKGROUND ART

Androgens are a generic name for C19. steroids. They are sex hormones important for the normal sexual differentiation and growth of males, masculinization at puberty, activation of initial spermatogenesis in the testes, and maintenance of male function. About 90% of androgens are produced by Leydig cells of the testes, the remaining, 10% by the adrenal gland, mainly as testosterone, and secreted into the blood. Testosterone is taken up into target cells, and converted by 5α-reductase into dihydrotestosterone (DHT) with potent biological activity. DHT, as well as testosterone, plays an important role in the development of male secondary sex characteristics (growth of sebaceous glands, acne, development of body hair, voice deepening, development of beards), growth of external genitalia (penis, testis), growth of sex accessory organs (prostate, seminal vesicles), sexual stimuli, and occurrence of erection.

In addition to these major actions, androgens have actions other than those on the reproductive system, such as protein anabolic action (increases in skeletal muscles mass and bone mass), suppression of gonadotropin secretion, and acceleration of erythropoiesis promoting action. Target cells for androgens are localized in external and sex accessory tissues, and are widely distributed in the brain, pituitary gland, muscular tissues, bones, and kidneys (N. Engl. J. Med. 334, 707–714, 1996).

In addition to these roles, androgens are reported to show an anti-inflammatory action. Recently, it is becoming clear that androgens attenuate arthritis and autoimmune disease by inhibiting the proliferation of inflammatory cells or suppressing the production of cytokines such as IL-6 (Ann. Rheum. Dis. 55, 811–815, 1996).

All androgenic actions are mediated through androgen receptor (hereinafter referred to as AR) having a molecular weight of about 100,000 which is present in the nuclei of target cells. The gene of AR was cloned by Chang and Lubahn et al. in 1988. Their study demonstrated that AR has a similar structure to estrogen, progesterone, mineral corticoid, and glucocortlcoid receptors, and they built a nuclear steroid receptor family (Science 240, 324–326, 327–330, 1988). Androgen with high liposolubility penetrate the target cell membrane by passive diffusion, and bind to the hormone-binding region of AR specifically and with high affinity to form dimmers, which bind to an androgen responsive DNA region (androgen response element: ARE) localized upstream from a particular gene. As a result, transcription of the target gene is initiated to induce the expression of mRNA, thereby producing a functional protein responsible for an androgenic action, thus exhibiting this action (Trend in Endocrinology and Metabolism 9, 317–324, 1998). In connection with this mechanism, compounds which bind to AR and show the same actions as natural ligands such as testosterone are defined as agonists, while compounds which inhibit their action are named antagonists.

The AR agonists used since olden days are injection drugs of testosterone esters (testosterone enanthate, testosterone propionate) with enhanced persistence after administration into the body, and oral drugs having a methyl group introduced at the 17α-position to protect the hydroxyl group at the 17β-position from inactivation due to its oxidation, thereby enhancing activity (i.e., methyltestosterone, fluoxymesterone). These preparations of androgen steroids are often used for target diseases at relatively large doses and for long periods. Thus, these preparations cause side effects, such as hepatic dysfunction, virilization, changes in the female vocal cord (male-like hoarseness), gastrointestinal disorder, euphoria, hypertrichosis of the body trunk, and alopecia. Especially androgen preparations having a methyl group at the 17α-position, have been reported to evoke serious hepatic dysfunction (N. Engl. J. Med. 334, 707–714, 1996). In recent years, nonsteroidal AR agonists, which attenuate the side effects of the steroids and are more selective for target tissues, have been under development. However, no compounds recognized throughout the world have been created.

As AR antagonists, steroidal anti-androgen preparations, such as chlormadinone acetate and cyproterone acetate, which are gestagen derivatives, have been used as therapeutic agents. It has been pointed out, however, that these steroid preparations accelerate the negative feedback mechanism of the hypothalamic-pituitary axis by their progesterone action, thereby lowering the blood testosterone level and decreasing sexual function and libido (Drugs Aging 5, 59–80, 1994).

To overcome them, flutamide and bicalutamide have been developed as nonsteroidal AR antagonists. Flutamide, an acylanilide derivative, is known to have no AR antagonistic action by itself, but produce activity when converted into hydroxyflutamide by substitution of a hydroxyl group for the α-carbon atom directly bonded to the carbonyl group as a result of metabolism. This hydroxyl group is presumed to be essential to the antagonistic action (J. Med. Chem. 31. 954–959, 1988). Flutamide is the nonsteroidal AR antagonist that became available clinically for the first time in the world. However, the blood half-life of its active metabolite is so short that a high dose should be administered three times daily, posing a problem of drug compliance (Clin. Pharmacokinet. 34, 405–417, 1998). Moreover, flutamide has been reported to cause side effects, such as diarrhea and serious hepatic disorders leading to death, thus hampering its clinical use (J. Urol. 57, 172–174, 1985; J. Urol. 155, 209–212, 1996).

Bicalutamide, an acylanilide derivative having a hydroxyl group at the α-carbon atom, is characterized with a stronger binding affinity for AR and a longer blood half-life (about 8 days) after administration, than hydroxyflutamide. Thus, bicalutamide can be administered once daily. However, tenderness and swelling of breasts, considered to be due to the action on central nervous system, occur frequently as side effects (J. New Remedies & Cinics 48, 307–321, 1999).

In animal experiments, it was reported that the conception rate of normal female rats mated to male rats administered flutamide and bicalutamide was decreased (The 80th Annual Meeting of The Endocrine Society, P3-126, June 24–27, New Orleans, La., 1998). Another problem with nonsteroidal AR antagonists is the occurrence of agonism during long-term use (J. Urol. 153, 1070–1072, 1995). Particularly in the treatment of prostatic cancer, the androgenic action needs to be blocked completely, so that the occurrence of the agonistic action raises a major problem in treatment.

In recent years, nonsteroidal AR antagonists with little effect on the central nervous system and the reproductive system and with potent AR antagonistic activity have been under development. However, no compounds recognized globally have been created.

The present invention has been accomplished in view of the therapies of and therapeutic researches on the diseases mediated through AR. The objects of the present invention are to provide novel nonsteroidal compounds and salts thereof, which have a specific and strong binding affinity for AR and exhibit AR agonism or antagonism; and to provide pharmaceuticals containing these, compounds or salts as active ingredients.

DISCLOSURE OF THE INVENTION

The inventors of the present invention conducted in-depth studies in an attempt to attain the above objects. As a result, they have found that tetrahydroquinoline derivatives have physiological activity mediated by AR, and have an excellent therapeutic effect on AR-mediated diseases. Based on this finding, they have accomplished this invention.

That is, the present invention relates to a tetrahydroqulnoline derivative represented by the following formula or salts thereof:

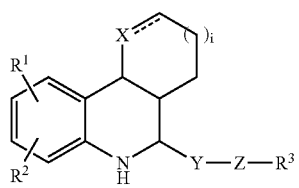

(I)

wherein $R^1$ and $R^2$ each independently represent a hydrogen atom, an alkyl group having 1–9 carbon atoms, an alkoxy group having 1–9 carbon atoms, a halogen atom, a nitro group, $NR^4R^5$ (wherein $R^4$ and $R^5$ each independently represent a hydrogen atom, an alkyl group having 1–9 carbon atoms, a cycloalkyl group having 3–7 carbon atoms, an aralkyl group having 7–9 carbon atoms, an aryl group, an aliphatic acyl group having 2–5 carbon atoms, an aliphatic acyloxy group having 2–5 carbon atoms, an aromatic acyl group, an aliphatic sulfonyl group having 1–4 carbon atoms, an aromatic sulfonyl group, an alkoxycarbonyl group having 2–5 carbon atoms, a hydroxyoxalyl group or an alkoxyoxalyl group having 3–7 carbon atoms), a carboxyl group, an alkoxycarbonyl group having 2–5 carbon atoms, an amido group, an alkylamido group having 2–5 carbon atoms, an alkylthio group having 1–4 carbon atoms, an aliphatic sulfinyl group having 1–4 carbon atoms, an aliphatic sulfonyl group having 1–4 carbon atoms, a cyano group, a sulfamoyl group, an aliphatic sulfamoyl group having 1–4 carbon atoms, an amidino group, a trifluoromethyl group, a trifluoromethoxy group or a tetrafluoroethoxy group; X represents CH, $CH_2$, O, S or $NR^6$ (wherein $R^6$ independently has the same meaning as $R^4$), provided that when X is CH, the dashed line in the formula signifies a double bond; 1 represents an integer of 0–2; Y represents an alkylene group having 1–9 carbon atoms that may optionally be substituted by an alkyl group having 1–9 carbon atoms, a cycloalkyl group having 3–7 carbon atoms, a hydroxyl group, an alkoxy group having 1–9 carbon atoms or $NR^7R^8$ (wherein $R^7$ and $R^8$ each independently have the same meaning as $R^4$); Z represents a single bond, —O—, —OCO—, —$OSO_2$—, —S—, —SCO—, —SO—, —$SO_2$—, —$NR^9$—, —$NR^9CO$—, —$NR^9SO_2$—, —$NR^9CONH$—, —$NR^9CSNH$—, —$NR^9COO$— or —$NR^9COCO$— (wherein $R^9$ represents a hydrogen atom, an alkyl group having 1–9 carbon atoms, a cycloalkyl group having 3–7 carbon atoms, an aralkyl group having 7–9 carbon atoms, an alkoxyalkyl group having 2–5 carbon atoms or an aryl group that may optionally be substituted by $R^{10}$ (wherein $R^{10}$ is an alkyl group having 1–9 carbon atoms, an alkoxy group having 1–9 carbon atoms, a halogen atom, a nitro group, an aryl group, $NR^{11}R^{12}$ (wherein $R^{11}$ and $R^{12}$ each independently have the same meaning as $R^4$), a carboxyl group, an alkoxycarbonyl group having 2–5 carbon atoms, an amido group, an alkylamido group having 2–5 carbon atoms, an alkylthio group having 1–4 carbon atoms, an aliphatic sulfinyl group having 1–4 carbon atoms, an aliphatic sulfonyl group having 1–4 carbon atoms, a cyano group, a sulfamoyl group, an aliphatic sulfamoyl group having 1–4 carbon atoms, a trifluoromethyl group, a trifluoromethoxy group or a tetrafluoroethoxy group)); $R^3$ represents a hydrogen atom, an alkyl group having 1–9 carbon atoms, a cycloalkyl group having 3–7 carbon atoms, an aralkyl group having 7–9 carbon atoms, an alkoxy group having 1–9 carbon atoms, an alkoxyalkyl group having 2–5 carbon atoms, a halogen atom, a substituted silyl group or an aryl group that may optionally be substituted by $R^{13}$ (wherein $R^{13}$ independently has the same meaning as $R^{10}$), provided that $R^3$ represents a halogen atom only when Z is a single bond. The present invention also relates to a pharmaceutical, a steroid receptor modulator, and an androgen receptor modulator, each containing the tetrahydroquinoline derivative of the formula (I) or salts thereof as the active ingredient.

BEST MODE FOR CARRYING OUT THE INVENTION

The substituents in the formula (I) will be described.

Examples of the "alkyl group having 1–9 carbon atoms" are straight chain or branched chain alkyl groups, such as a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, an n-hexyl group, a 3.3-dimethylbutyl group, a 2-ethylbutyl group, an n-heptyl group, a 2-methylhexyl group, an n-octyl group, a 2-propylpentyl group, and an n-nonyl group.

Examples of the "alkoxy group having 1–9 carbon atoms" are straight chain or branched chain alkoxy groups, such as a methoxy group, an ethoxy group, an n-propoxy group, an isopropoxy group, an n-butoxy group, an isobutoxy group, a tert-butoxy group, a sec-butoxy group, an n-pentyloxy group, a tert-amyloxy group, a 3-methylbutoxy group, a neopentyloxy group, an n-hexyloxy group, a 3,3-dimethylbutoxy group, a 2-ethylbutoxy group, an n-heptyloxy group, a 2-methylhexyloxy group, an n-octyloxy group a 2-propylpentyloxy group, and an n-nonyloxy group.

Examples of the "halogen atom" are a fluorine atom, a chlorine atom, a bromine atom, and an iodine atom.

Examples of the "cycloalkyl group having 3–7 carbon atoms" are a cyclopropyl group, a cyclobutyl group, a cyclopentyl group, a cyclohexyl-group, and a cycloheptyl group.

Examples of the "aralkyl group having 7–9 carbon atoms" are a benzyl group, a phenethyl group, and a phenylpropyl group.

Examples of the "aryl group" are a phenyl group, a 1-naphthyl group, and a 2-naphthyl group.

Examples of the "aliphatic acyl group having 2–5 carbon atoms" are straight chain or branched chain aliphatic acyl groups, such as an acetyl group, a propionyl group, a butyryl group, an isobutyryl group, a valeryl group, an isovaleryl group, and a pivaloyl group.

Examples of the aliphatic acyloxy group having 2–5 carbon atoms are straight chain or branched chain aliphatic acyloxy groups, such as an acetoxy group, a propionyloxy group, a butyryloxy group, an isobutyryloxy group, a valeryloxy group, an isovaleryloxy group, and a pivaloyloxy group.

Examples of the "aromatic acyl group" are a benzoyl group and a toluoyl group.

Examples of the aliphatic sulfonyl group having 1–4 carbon atoms are straight chain or branched chain aliphatic sulfonyl groups, such as a methanesulfonyl group, an ethanesulfonyl group, an n-propylsulfonyl group, an isopropylsulfonyl group, an n-butylsulfonyl group, an isobutylsulfonyl group, a tert-butylsulfonyl group, and a sec-butylsulfonyl group.

Examples of the "aromatic sulfonyl group" are a benzenesulfonyl group and a toluenesulfonyl group.

Examples of the "alkoxycarbonyl group having 2–5 carbon atoms" are straight chain or branched chain alkoxycarbonyl groups, such as a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, and a sec-butoxycarbonyl group.

Examples of the "alkoxyoxalyl group having 3–7 carbon atoms" are straight chain or branched chain alkoxyoxalyl groups, such as a methoxyoxalyl group, an ethoxyoxalyl group, an n-propoxyoxalyl group, an isopropoxyoxalyl group, an n-butoxyoxalyl group, an isobutoxyoxalyl group, a tert-butoxyoxalyl group, a sec-butoxyoxalyl group, an n-pentyloxyoxalyl group, a 3-methylbutoxyoxalyl group, and a neopentyloxyoxalyl group.

Examples of the "alkylamido group having 2–5 carbon atoms" are straight chain or branched chain alkylamido groups, such as a methylamido group, an ethylamido group, an n-propylamido group, an isopropylamido group, an n-butylamido group, an isobutylamido group, a tert-butylamido group, a sec-butylamido group, an n-pentylamido group, and a tert-amylamido group.

Examples of the "alkylthio group having 1–4 carbon atoms" are straight chain or branched chain alkylthio groups, such as a methylthio group, an ethylthio group, an n-propylthio group, an isopropylthio group, an n-butylthio group, an isobutylthio group, a tert-butylthio group, and a sec-butylthio group.

Examples of the "aliphatic sulfinyl group having 1–4 carbon atoms" are straight chain or branched chain aliphatic sulfinyl groups, such as a methanesulfinyl group, an ethanesulfinyl group, an n-propylsulfinyl group, an isopropylsulfinyl group, an n-butylsulfinyl group, an isobutylsulfinyl group, a tert-butylsulfinyl group, and a sec-butylsulfinyl group.

Examples of the "aliphatic sulfonyl group having 1–4 carbon atoms" are straight chain or branched chain aliphatic sulfonyl groups, such as a methanesulfonyl group, an ethanesulfonyl group, an n-propylsulfonyl group, an isopropylsulfonyl group, an n-butylsulfonyl group, an isobutylsulfonyl group, a tert-butylsulfonyl group, and a sec-butylsulfonyl group.

Examples of the "aliphatic sulfamoyl group having 1–4 carbon atoms" are straight chain or branched chain aliphatic sulfamoyl groups, such as a methanesulfamoyl group, an ethanesulfamoyl group, an n-propylsulfamoyl group, an isopropylsulfamoyl group, an n-butylsulfamoyl group, an isobutylsulfamoyl group, a tert-butylsulfamoyl group, and a sec-butylsulfamoyl group.

Examples of the "alkylene group having 1 to 9 carbon atoms" are a methylene group, an ethylene: group, a tetramethylene group, a pentamethylene group, and a hexamethylene group.

Examples of the "alkoxyalkyl group having 2–5 carbon atoms" are straight chain or branched chain alkoxy groups, such as a methoxymethyl group, an ethoxymethyl group, an n-propoxymethyl group, an isopropoxymethyl group, an n-butoxymethyl group, an isobutoxymethyl group, a tert-butoxymethyl group, a sec-butoxymethyllgroup, a methoxyethyl group, an ethoxyethyl group, an n-propoxyethyl group, an isopropoxyethyl group, a methoxypropyl group, an ethoxypropyl group, and a methoxybutyl group.

Examples of the "substituted silyl group" are a trimethylsilyl group, a triethylsilyl group, a triisopropylsilyl group, a dimethylisopropylsilyl group, a tert-butyldimethylsilyl group, a tert-butyldiphenylsilyl group, and a triphenylsilyl group.

If asymmetric carbon is present in the compound of the present invention represented by the formula (I), its racemic compounds, diastereomers, and individual optical isomers are all included in the present invention. If its geometrical isomers are present, (E) compounds, (Z) compounds, and mixtures of them are all included in the present invention.

The salts of the compounds represented by the formula (I) are not limited, as long as they are those which are pharmacologically acceptable. Their examples include hydrohalogenic acid salts, such as hydrofluorides, hydrochlorides, hydrobromides, and hydroiodides, inorganic acid salts, such as nitrates, perchlorates, sulfates, phosphates, and carbonates, lower alkylsulfonic acid salts, such as methanesulfonates, trifluoromethanesulfonates, and ethanesulfonates, arylsulfonic acid salts, such as benzenesulfonates and p-toluenesulfonates, carboxylic acid salts, such as acetates, fumarates, succinates, citrates, tartrates, oxalates, and maleates, amino acid salts, such as glycine salts, alanine salts, glutamates, and aspartates, and alkali metal salts, such as sodium salts and potassium salts. Examples of the solvates are solvates with solvents, such as acetone, 2-butanol, 2-propanol, ethanol, ethyl acetate, tetrahydrofuran, and dlethyl ether.

The tetrahydroquinoline derivative of the present invention can be produced by the following methods:

[Production Method 1]

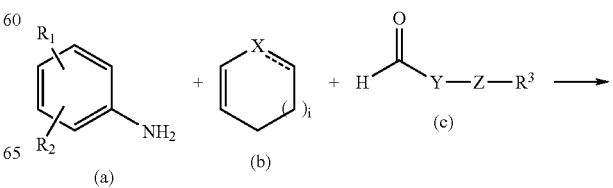

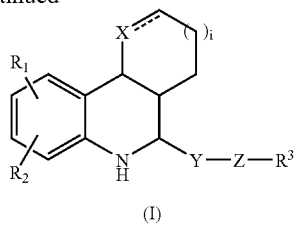

(I)

where all the symbols are as defined above, except for cases where —Z—$R^3$ represents SH, $SOR^3$, $SO_2R^3$ and $NH_2$.

The compound of the present invention, expressed by the formula (I), can be produced by reacting the compounds represented by the formulas (a), (b) and (c) in an inert solvent in the presence or absence of an acid.

The compounds represented by the formulas (a), (b) and (c) can be obtained as commercially available reagents, or by easy derivation therefrom by routine chemical reactions.

The present reaction will be described concretely. Any type of acids, organic or inorganic, are preferred. For example, acetic acid, trifluoroacetic acid, p-toluenesulfonic acid, hydrochloric acid, sulfuric acid, tin tetrachloride, titanium tetrachloride, boron trifluoride diethyl etherate, diethylaluminum chloride, or ethylaluminum dichloride is used. The acid is preferably used in an amount of a catalytic amount to 10 equivalents with respect to the compound represented by the formula (a). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water or a mixture of these solvents. The reaction temperature is preferably −20 to 100° C., and the reaction time is preferably 5 minutes to 48 hours.

[Production Method 2]

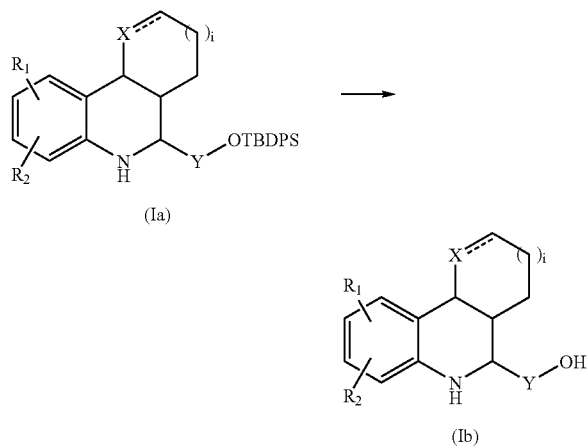

where TBDPS signifies a tert-butyldiphenylsilyl group, and the other symbols are as defined earlier.

Of the compounds of the present invention, the compound represented by the formula (Ib) can be produced by deprotection of the compound represented by the formula (Ia) by means of hydrolysis in the presence of an acid or a base or treatment with a fluoride, in addition to the method shown in Production Method 1.

The present reaction will be described concretely. Any type of acids, organic or inorganic, are preferred. For example, acetic acid, trifluoroacetic acid, hydrochloric acid, or sulfuric acid is used. Either type of bases, metal hydroxides or metal carbonates, are preferred. For example, sodium hydroxide, potassium hydroxide, barium hydroxide, sodium carbonate, or potassium carbonate is used. As the fluoride, an aqueous hydrogen fluoride solution, or tetrabutylammonium fluoride, for example, is used. The acid, base or fluoride is preferably used in an amount of 1 to 50 equivalents with respect to the compound represented by the formula (Ia). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water or a mixture of these solvents. The reaction temperature is preferably 0 to 100° C., and the reaction time is preferably 30 minutes to 24 hours.

[Production Method 3]

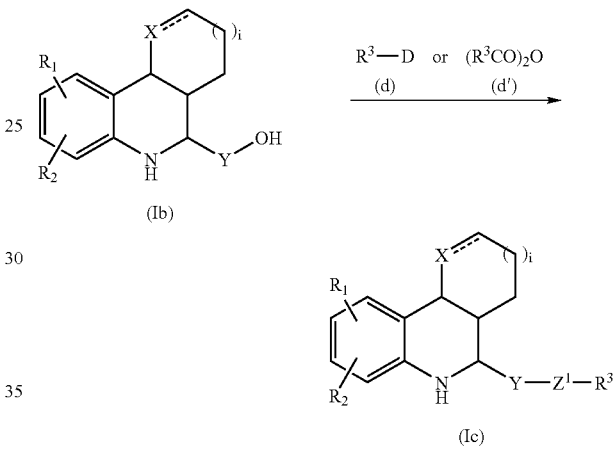

where D represents a chlorosulfonyl group or a halogenated carbonyl group, $Z^1$ represents —OCO— or —$OSO_2$—, and the other symbols are as defined earlier.

Of the compounds of the present invention, the compound represented by the formula (Ic) can be produced by reacting the compound represented by the formula (Ib) with the compound represented by the formula (d) or (d') without a solvent or in an inert solvent in the presence or absence of a base.

Examples of the "halogenated carbonyl group" are a chlorocarbonyl group and a bromocarbonyl group.

The present reaction will be described concretely. The base is preferably a tertiary amine, and its examples are triethylamine and pyridine. The compound represented by the formula (d) or (d') is preferably used in an amount of 1 to 10 equivalents with respect to the compound represented by the formula (Ib). The base is preferably used in an amount of 1 equivalent to a large excess with respect to the compound represented by the formula (d) or (d'). The reaction solvent is not limited, as long as it is a solvent which does not markedly impede the present reaction. The preferred reaction solvent, is dichloromethane, chloroform, 1,2-dichloroethane, 1,1,2,2-tetrachloroethane, toluene, dimethylformamide, or tetrahydrofuran. The reaction temperature is preferably 0 to 80° C., and the reaction time is preferably; 30 minutes to 12 hours.

[Production Method 4]

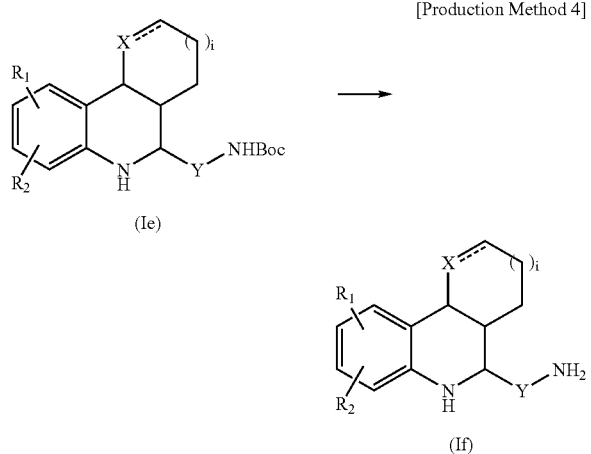

where Boc represents a tert-butoxycarbonyl group, and the other symbols are as defined earlier.

Of the compounds of the present invention, the compound represented by the formula (If) can be produced by deprotection of the compound represented by the formula (Ie) by means of treatment with an acid.

The present reaction will be described concretely. Any type of acids, organic or inorganic, are preferred. For example, acetic acid, trifluoroacetic acid, p-toluenesulfonic acid, hydrochloric acid, or sulfuric acid is used. The acid is preferably used in an amount of 1 to 50 equivalents with respect to the compound represented by the formula (Ie). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water, or a mixture of these solvents. The reaction temperature is preferably 0 to 100° C., and the reaction time is preferably 30 minutes to 24 hours.

[Production Method 5]

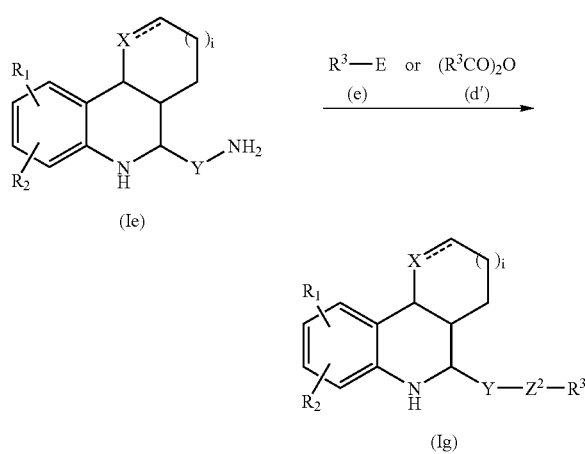

where E represents a chlorosulfonyl group, a halogenated arbonyl group, an isocyanato group, or a thlolsocyanato group, $Z^2$ represents —NHCO—, —NHSO$_2$—, —NHCONH—, or —NHCSNH—, and the other symbols are as defined earlier.

Of the compounds of the present invention, the compound represented by the formula (Ig) can be produced by reacting the compound represented by the formula (If) with the compound represented by the formula (e) or (d') without a solvent or in an inert solvent in the presence or absence of a base.

Examples of the "halogenated carbontyl group" are a chlorocarbonyl group and a bromocarbonyl group.

The present reaction will be described concretely. The base is preferably a tertiary amine, and its examples are triethylamine and pyrldlne. The compound represented by the formula (e) or (d') is preferably used in an amount of 1 to 10 equivalents with respect to th e compound represented by the formula (If). The base is preferably used in an amount of 1 equivalent to a large excess with respect to the compound represented by the formula (e) or (d'). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 0 to 80° C., and the reaction time is preferably 30 minutes to 12 hours.

[Production Method 6]

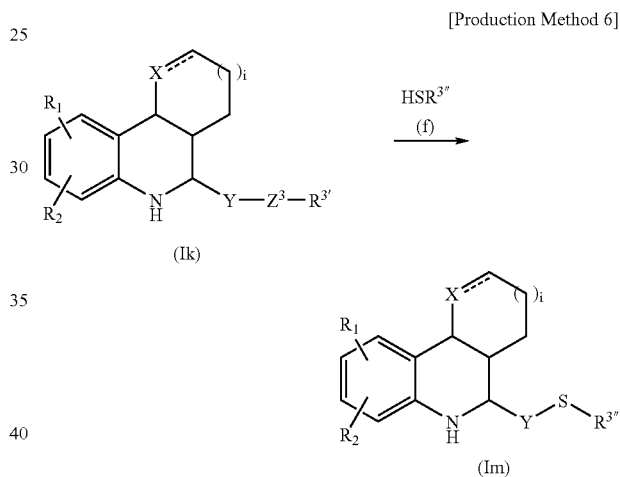

where $Z^3$ represents a single bond, $R^3$ represents a halogen atom, $R^{3''}$ represents $R^3$ other than a halogen atom, and the other symbols are as defined earlier.

Of the compounds of the present invention, the compound represented by the formula (Im) can be produced by reacting the compound represented by the formula (Ik) with the compound represented by the formula (f) without a solvent or in an inert solvent in the presence or absence of a base.

The present reaction will be described concretely. The base is, for example, triethylamine, pyridine, sodium hydride, or potassium tert-butoxide. The compound represented by the formula (f) is preferably used in an amount of 1 to 10 equivalents with respect to the compound represented by the formula (Ik). The base is preferably used in an amount of 1 equivalent to a large excess with respect to the compound represented by the formula (f). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 0 to 100° C., and the reaction time is preferably 5 minutes to 24 hours.

[Productcion Method 7]

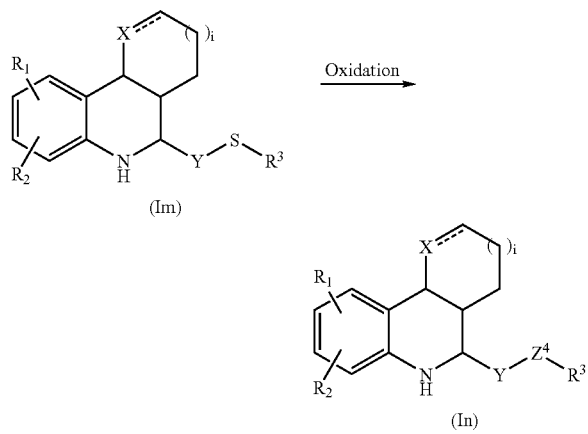

Oxidation where $Z^4$ represents —SO— or —SO$_2$—, and the other symbols are as defined earlier.

Of the compounds of the present invention, the compound represented by the formula (In) can be produced by oxidizing the compound represented by the formula (Im) in an inert solvent in the presence of an oxidizing agent.

The present reaction will be described concretely. As the oxidizing agent, peracetic acid or m-chlorobenzolc acid, for example, is named. The oxidizing agent is preferably used in an amount of 1 equivalent to a large excess with respect to the compound represented by the formula (Im). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 20 to 100° C., and the reaction time is preferably 5 minutes

[Production Method 8]

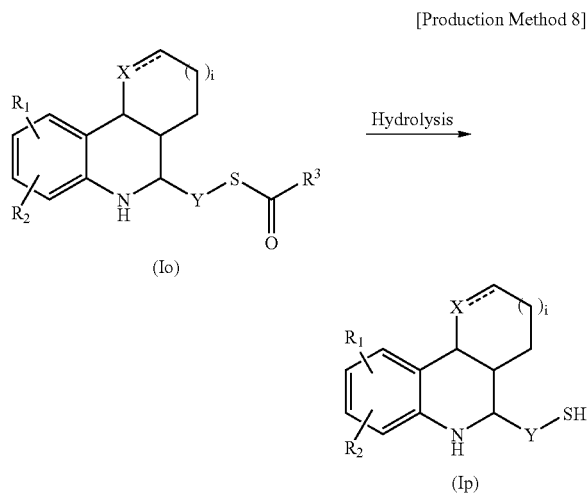

Hydrolysis where all the symbols are as defined earlier.

Of the compounds of the present invention, the compound represented by the formula (Ip) can be produced by hydrolyzing the compound represented by the formula (Io) in the usual manner in the presence of an acid or a base.

The present reaction will be described concretely. Any type of acids, organic or inorganic, are preferred. For example, acetic acid, trifluoroacetic acid, hydrochloric acid, or sulfuric acid is named. Either type of bases, metal hydroxides or metal carbonates, are preferred. For example, sodium hydroxide, potassium hydroxide, barium hydroxide, sodium carbonate, or potassium carbonate is named. The acid or base is preferably used in an amount of 1 to 50 equivalents with respect to the compound represented by the formula (Io). The reaction solvent is not limited, as long as it is a solvent which does not markedly impede the present reaction. The preferred reaction solvent is water, methanol, ethanol, tetrahydrofuran, dioxane, chloroform, 1,2-dichloroethane, or a mixture of these solvents. The reaction temperature is preferably 0 to 100° C., and the reaction time is preferably 30 minutes to 24 hours.

The compounds of the present invention, which are produced by the above-described methods, are isolated and purified as free compounds, their salts, various solvates thereof, such as hydrates or ethanolates, or crystalline polymorphic substances. The pharmacologically acceptable salts of the compounds according to the present invention can be produced by the general salt-forming reaction. The isolation and purification are performed by applying chemical operations, such as extractive fractionation, crystallization, and various chromatographic techniques. The stereochemically pure optical isomers can be synthesized by using suitable starting compounds, or by optical resolution of racemic compounds.

The tetrahydroquinoline derivatives,or salts thereof according to the present invention have anexcellent steroid receptor modulating action and an excellent AR modulating action. These substances can be used as active ingredients to form pharmaceuticals, steroid receptor modulators, or AR modulators. These agents can be widely used in the prophylaxis and treatment of various dependent diseases.

As the AR-dependent diseases, the following categories A and B are named:

A. Diseases which can be expected to be cured by the physiological action of androgen: Examples,include male hypogonadism, male sexual dysfunction (impotence, male dysspermatogenic sterility), abnormal sex differentiation (male hermaphroditism), male delayed puberty, male infertility, aplastic anemia, hemolytic anemia, sicklemia anemia, idiopathic nonthrombocytopenic purpura, myslofibrosis, renal anemia, wasting diseases (after operation, malignant tumor, trauma, chronic renal disease, burns, AIDS infection), osteoporosis, abatement of pain in terminal carcinoma of female genitalia, inoperable breast cancer, mastopathy, endometriosis, and female sexual dysfunction.

B. Diseases for which androgen is a precipitating factor: Examples include prostatic cancer, prostatomeegaly, virilization, acne, seborrhea, hypertrichosis, alopecia, male precocious puberty, and polycystic ovary syndrome.

For the category A diseases, the compounds of the present invention with AR agonistic action can be used, their examples being compounds of Examples 1, 23, 25, 39, 56, 60, 65, 66 and 67 to be described later.

For the category B diseases, the compounds of the present invention with AR antagonistic action can be used, their examples being compounds of Examples 6, 7, 8, 9, 13, 19. 20, 21, 29, 35. 40, 53 and 62 to be described later.

The pharmaceuticals of the present invention can be applied widely to these AR-dependent diseases, and may be applied to diseases which are not exemplified here, if the modulation of AR function is required for them at present or in the future.

The pharmaceuticals of the present invention can be administered orally or parenterally, and may be of the systemic administration type or local administration type.

Their dosage forms are not limited, and can be selected, as desired, according to the route of administration. Their examples include tablets, capsules, sugar-coated tablets, granules, subtle granules, inhalations, suppositories, liquids and solutions, syrups, dry syrups, suspensions, emulsions, lotions, ointments, patches, sprays, gels, nasal drops, eye drops, and injections.

These preparations can be produced by incorporating organic or inorganic, solid or liquid vehicles, adjuvants, stabilizers, wetting agents, emulsifying agents, buffers, and other pharmacologically acceptable various additives.

The dose of the pharmaceutical of the present invention in humans is determined, as desired, according to various conditions, such as the purpose of treatment or prevention, the patient's sex, body weight, age, and health, the type and severity of the disease, dosage form, the route of administration, and the duration of treatment. The daily dose of the tetrahydroquinoline derivative of the present invention is generally 0.01 to 100 mg/kg.

The pharmaceuticals of the present invention may be used in the treatment of androgen receptor-mediated diseases in warm-blooded animals, such as domestic animals, pets, bred animals, or wild animals. The dosage forms and doses in this case can be determined by reference to the dosage forms and doses in humans.

The compounds of the present invention and the methods for their production will be described in further detail by working examples. However, the present invention is not to be interpreted restrictedly because of these descriptions.

$^1$H—NMR spectra were recorded on JNM-EX270 Spectrometer (270 MHz, JEOL Ltd.). Chemical shifts (δ) are expressed in ppm downfield from tetramethylsilane (TMS).

In the structural formulas and tables offered below, Me represents a methyl group, Et an ethyl group, Pr a propyl group, Bu a butyl group, Ph a phenyl group, Bn a benzyl group, and Ac an acetyl group.

EXAMPLE 1

Production of 2-methyl-2-(8-nitro-3a,4,5,9b-tetrahydro-3H-cyclopenta[c]quinolin-4-yl)-propan-1-ol

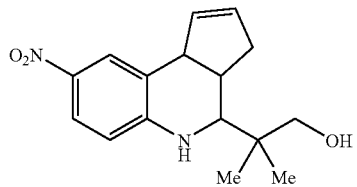

4-Nitroaniline (9.8 g), 6.5 ml of cyclopentadiene, and 5.5 ml of trifluoroacetic acid were dissolved in 70 ml of acetonitrile, and 10.0 g of hydroxypivalaldehyde was added at 0° C. After 30 minutes stirring at room temperature, the reaction mixture was concentrated under reduced pressure. The residue was purified by silica gel column chromatography (elution solvent: hexane:ethyl acetate=1:1) to obtain 4.8 g of the captioned compound. Its physical properties are shown below.

$^1$H-NMR (CDCl$_3$) δ: 7.85 (s, 1H), 7.84 (d, J=8.9 Hz, 1H), 6.47 (d, J=8.9 Hz, 1H), 5.96 (brs, 1H), 5.78 (brs, 1H), 3.98 (d, J=9.9 Hz, 1H), 3.64 (d, J=10.6 Hz, 1H), 3.55 (d, J=10.6 Hz, 1H), 3.54 (d, J=2.3 Hz, 1H), 2.87 (ddt, J=2.3, 8.2, 9.9 Hz, 1H), 2.48 (dd, J=9.9, 15.5 Hz, 1H), 2.26 (dd, J=8.2, 15.5 Hz, 1H), 1.11 (s, 3H), 0.96 (s, 3H).

Compounds shown in Examples 2 to 34 were synthesized by using similar method of Example 1. The physical properties of the resulting compounds are shown in Tables 1 to 4.

TABLE 1

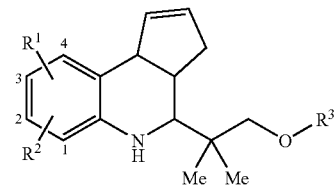

| Ex. No. | R$^1$ | R$^2$ | R$^3$ | $^1$H-NMR δ: |
|---|---|---|---|---|
| 2 | 3-NO$_2$ | H | TBDPS | (CDCl$_3$): 7.86(d, J=2.6Hz, 1H), 7.78(dd, J=2.6, 8.9Hz, 1H), 7.48–7.30(m, 6H), 6.19(d, J=8.9Hz, 1H), 5.95(d, J=2.6Hz, 1H), 5.92(s, 1H), 5.77(brs, 1H), 3.97(d, J=6.3Hz, 1H), 3.61(d, J=9.9Hz, 1H), 3.55(d, J=2.0Hz, 1H), 3.44(d, J=9.9Hz, 1H), 2.83(dt, J=10.2, 6.3Hz, 1H), 2.47(dd, J=10.2, 13.5Hz, 1H), 2.22(ddd, J=2.6, 6.3, 13.5Hz, 1H), 1.14(s, 9H), 1.11(s, 3H), 0.87(s, 3H). |
| 3 | 3-CN | H | TBDPS | (CDCl$_3$): 7.70–7.60(m, 4H), 7.48–7.34(m, 6H), 7.11(d, J=8.3Hz, 1H), 6.27(d, J=8.3Hz, 1H), 5.86(brs, 1H), 5.75(brs, 1H), 3.93(d, J=7.3Hz, 1H), 3.59(d, J=9.9Hz, 1H), 3.49(d, J=1.7Hz, 1H), 3.41(d, J=9.9Hz, 1H), 2.81(dt, J=9.9, 7.3Hz, 1H), 2.49(dd, J=9.9, 15.8Hz, 1H), 2.19(dd, J=7.3, 15.8Hz, 1H), 1.12(s, 9H), 1.09(s, 3H), 0.85(s, 3H). |
| 4 | 3-NO$_2$ | 1-OH | TBDPS | (CDCl$_3$): 7.64(d, J=6.3Hz, 4H), 7.46–7.30(m, 7H), 6.52(d, J=8.6Hz, 1H), 5.72–5.62(m, 2H), 4.77(d, J=8.9Hz, 1H), 3.53–3.40(m, 4H), 3.02–2.91(m, 1H), 2.61–2.51(m, 1H), 2.23–2.12(m, 1H), 1.08(s, 9H), 1.06(s, 3H), 0.85(s, 3H). |
| 5 | 2-NO$_2$ | 1-OH | TBDPS | (CDCl$_3$): 7.73–7.55(m, 5H), 7.46–7.31(m, 7H), 5.95(brs, 1H), 5.75–5.73(m, 1H), 5.69 (brs, 1H), 3.97(d, J=7.6Hz, 1H), 3.60(brs, 1H), 3.55(d, J=10.2Hz, 1H), 3.46(d, J=10.2Hz, 1H), 2.87(q, J=8.6Hz, 1H), 2.52–2.43(m, 1H), 2.25–2.16(m, 1H), 1.09(s, 9H), 1.07(s, 3H), 0.93(s, 3H). |
| 6 | 3-NO$_2$ | H | CH$_2$OMe | (CDCl$_3$): 7.86(s, 1H), 7.84(d, J=8.6Hz, 1H), 6.45(d, J=8.6Hz, 1H), 5.96(ddd, J=1.7, 2.3, 5.6Hz, 1H), 5.77(dd, J=1.0, 5.6Hz, 1H), 5.65(s, 1H), 4.68(d, J=6.6Hz, 1H), 4.63(d, J=6.6Hz, 1H), 3.99(d, J=8.3Hz, 1H), 3.52(d, J=2.0Hz, 1H), 3.49(d, J=2.0Hz, 1H), 3.36 (s, 3H), 3.35(d, J=9.2Hz, 1H), 2.87(dt, J=10.2, 8.3Hz, 1H), 2.48(ddd, J=2.3, 10.2, 15.5Hz, 1H), 2.26(ddd, J=1.7, 8.3, 15.5Hz, 1H), 1.11(s, 3H), 1.00(s, 3H). |

TABLE 1-continued

| Ex. No. | R¹ | R² | R³ | ¹H-NMR δ: |
|---|---|---|---|---|
| 7 | 4-NO₂ | H | H | (CDCl₃): 7.12(dd, J=1.3, 8.3Hz, 1H), 7.00(t, J=8.3Hz, 1H), 6.74 (dd, J=1.3, 8.3Hz, 1H), 5.73(dd, J=1.7, 4.3Hz, 1H), 5.62(ddd, J=1.7, 2.3, 4.3Hz, 1H), 5.13(s, 3H), 4.65(d, J=7.3Hz, 1H), 3.59(d, J=10.9Hz, 1H), 3.54 (d, J=10.9Hz, 1H), 3.41(d, J=2.3Hz, 1H), 2.95(dt, J=2.3, 9.9, 7.3Hz, 1H), 2.59(ddd, J=2.3, 9.9, 15.8Hz, 1H), 2.22(ddd, J=1.7, 7.3, 15.8Hz, 1H), 1.08 (s, 3H), 0.97(s, 3H). |
| 8 | 4-CN | H | H | (CDCl₃): 6.98(d, J=4.6Hz, 2H), 6.75(t, J=4.6Hz, 1H), 6.20(brs, 1H), 5.77(brs, 1H), 4.24(d, J=8.3Hz, 1H), 3.55(s, 2H), 3.30(s, 1H), 3.02(dq, J=2.3, 8.3Hz, 1H), 2.65(dd, J=8.3, 15.5Hz, 1H), 2.28(dd, J=8.3, 15.5Hz, 1H), 1.09(s, 3H), 0.97(s, 3H). |
| 9 | 3-NO₂ | H | Me | (CDCl₃): 7.86–7.82(m, 2H), 6.44(d, J=9.6Hz, 1H), 5.96(ddd, J=1.7, 3.0, 5.9Hz, 1H), 3.97(d, J=8.3Hz, 1H), 3.49(d, J=1.7Hz, 1H), 3.38(s, 3H), 3.35(d, J=9.2Hz, 1H), 3.18(d, J=9.2Hz, 1H), 2.84(dt, J=10.2, 8.3Hz, 1H), 2.47(ddd, J=2.3, 10.2, 15.8Hz, 1H), 2.24(dd, J=8.3, 15.8Hz, 1H), 1.09(s, 3H), 0.96 (s, 3H). |
| 10 | 3-CN | H | Me | (CDCl₃): 7.18–7.15(m, 2H), 6.47(d, J=8.9Hz, 1H), 5.87(ddd, J=1.7, 3.0, 5.6Hz, 1H), 5.75(dd, J=1.3, 4.3Hz, 1H), 5.44(s, 1H), 3.92(d, J=8.3Hz, 1H), 3.42(d, J=2.3Hz, 1H), 3.36(s, 3H), 3.32 (d, J=8.9Hz, 1H), 3.17(d, J=8.9Hz, 1H), 2.82(dt, J=9.9, 8.3Hz, 1H), 2.49(ddd, J=2.3, 9.9, 15.8Hz, 1H), 2.21(ddd, J=1.3, 8.3, 15.8Hz, 1H), 1.07(s, 3H), 0.93(s, 3H). |
| 11 | 3-NO₂ | H | Et | (CDCl₃): 7.86(s, 1H), 7.84(d, J=9.9Hz, 1H), 6.40(d, J=9.9Hz, 1H), 6.15(s, 1H), 5.96–5.95(m, 1H), 5.77(d, J=7.9Hz, 1H), 3.97(d, J=7.9Hz, 1H), 3.54–3.44(m, 3H), 3.38(d, J=8.9, 1H), 3.23(d, J=8.9Hz, 1H), 2.84(dt, J=10.2, 7.9Hz, 1H), 2.47(ddd, J=2.3, 10.2, 15.8Hz, 1H), 2.24(dd, J=7.9, 15.8Hz, 1H), 1.26(t, J=6.9Hz, 3H), 1.10(s, 3H), 0.94(s, 3H). |
| 12 | 3-CN | H | Et | (CDCl₃): 7.18–7.15(m, 2H), 6.43(d, J=8.9Hz, 1H), 5.86(t, J=2.6Hz, 1H), 5.76–5.72(m, 2H), 3.92(d, J=7.6Hz, 1H), 3.48(q, J=6.9Hz, 2H), 3.40(d, J=2.0Hz, 1H), 3.35(d, J=8.9Hz, 1H), 3.20(d, J=8.9Hz, 1H), 2.82(dt, J=10.2, 7.6Hz, 1H), 2.50(ddd, J=2.0, 10.2, 15.8Hz, 1H), 2.22(ddd, J=1.0, 7.6, 15.8Hz, 1H), 1.24(t, J=6.9Hz, 3H), 1.08(s, 3H), 0.92(s, 3H). |
| 13 | 3-NO₂ | H | Bn | (CDCl₃): 7.84(s, 1H), 7.81(d, J=8.9Hz, 1H), 7.42–7.29(m, 5H), 6.23(d, J=8.9Hz, 1H), 5.97 (s, 1H), 5.95(ddd, J=1.7, 2.3, 5.6Ha, 1H), 5.75(d, J=5.6Hz, 1H), 4.52(s, 2H), 3.97(d, J=8.2Hz, 1H), 3.51(d, J=2.3Hz, 1H), 3.46(d, J=8.9Hz, 1H), 3.32(d, J=8.9Hz, 1H), 2.84(dt, J=9.9, 8.2Hz, 1H), 2.46(ddd, J=2.3, 9.9, 15.8Hz, 1H), 2.23 (dd, J=8.2, 15.8Hz, 1H), 1.12 (s, 3H), 0.96(s, 3H). |
| 14 | 3-CN | H | Bn | (CDCl₃): 7.41–7.27(m, 5H), 7.17(s, 1H), 7.13(d, J=8.3Hz, 1H), 6.28(d, J=8.3Hz, 1H), 5.85 (ddd, J=1.3, 2.0, 5.6Ha, 1H), 5.74(d, J=5.6Hz, 1H), 5.55(s, 1H), 4.51(s, 2H), 3.92(d, J=8.3Hz, 1H), 3.52–3.49(m, 2H), 3.30(d, J=8.9Hz, 1H), 2.82(dt, J=9.9, 8.3Hz, 1H), 2.48(ddd, J=2.0, 9.9, 15.5Hz, 1H), 2.21 (ddd, J=1.3, 8.3, 15.5Hz, 1H), 1.10(s, 3H), 0.94(s, 3H). |
| 15 | 3-COOH | H | H | (DMSO-d₆): 11.97(s, 1H), 7.47 (s, 1H), 7.41(d, J=8.3Hz, 1H), 6.67(d, J=8.3Hz, 1H), 5.91(brs, 1H), 5.66(brs, 1H), 4.93(brs, 1H), 3.90(d, J=78.3Hz, 1H), 3.36–3.26(m, 3H), 2.77(dd, J=8.3, 17.5Hz, 1H), 2.63–2.27(m, 1H), 2.18(dd, J=8.3, 14.4Hz, 1H), 0.94(s, 3H), 0.88 (s, 3H). |
| 16 | 3-SMe | H | H | (CDCl₃): 7.01(s, 1H), 7.00–6.95(m, 1H), 6.53(d, J=8.3Hz, 1H), 5.92–5.86(m, 1H), 5.75–5.72(m, 1H), 3.96–3.92(m, 1H), 3.58(d, J=11.0Hz, 2H), 3.49(d, J=11.0Hz, 1H), 3.35(d, J=1.7Hz, 1H), 2.86(ddd, J=2.3, 8.3, 18.0Hz, 1H), 2.65–2.52(m, 1H), 2.40(s, 3H), 2.31–2.21(m, 1H), 1.05(s, 3H), 1.00(s, 3H). |
| 17 | 3-SOMe | H | H | (CDCl₃): 7.27–7.23(m, 1H), 7.16(dt, J=1.7, 8.3Hz, 1H), 6.57 (dd, J=8.3, 12.0Hz, 1H), 5.90 (brs, 1H), 5.74(brs, 1H), 3.99(d, J=7.9Hz, 1H), 3.53(s, 1H), 3.52 (s, 1H), 3.42(d, J=4.0Hz, 1H), 2.92–2.81(m, 1H), 2.67(s, 3H), 2.60–2.49(m, 1H), 2.29–2.20 (m, 1H), 1.08(s, 3H), 0.95(s, 3H). |
| 18 | 3-SO₂Me | H | H | (CDCl₃): 7.45–7.39(m, 2H), 6.55(d, J=8.6Hz, 1H), 5.92(brs, 1H), 5.76(brs, 1H), 3.99(brs, 1H), 3.57–3.47(m, 1H), 2.98 (s, 3H), 2.98–2.85(m, 1H), 2.56–2.45(m, 1H), 2.29–2.19(m, 1H), 1.26(s, 3H), 1.09 (s, 3H). |

TABLE 2

| Ex. No. | R¹ | R³ | ¹H-NMR (CDCl₃) δ: |
|---|---|---|---|
| 19 | NO₂ | Me | 7.88–7.84(m, 2H), 6.54(d, J=9.2Hz, 1H), 5.99–5.97(m, 1H), 5.78–5.76(m, 1H), 4.84(brs, 1H), 4.02(d, J=8.3Hz, 1H), 3.63(d, J=2.6Hz, 1H), 3.23(s, 3H), 2.81–2.75(m, 1H), 2.51–2.42(m, 1H), 2.22–2.16(m, 1H), 1.27(s, 3H), 1.22(s, 3H). |
| 20 | CN | Me | 7.21(s, 1H), 7.19(d, J=8.6Hz, 1H), 6.55(d, J=8.6Hz, 1H), 5.91–5.89(m, 1H), 5.77–5.75(m, 1H), 4.53(brs, 1H), 3.96(d, J=8.3Hz, 1H), 3.57(d, J=2.2Hz, 1H), 3.22(s, 3H), 2.85–2.71(m, 1H), 2.52–2.43(m, 1H), 2.22–2.14(m, 1H), 1.25(s, 3H), 1.21(s, 3H). |
| 21 | NO₂ | Bn | 7.88–7.82(m, 2H), 7.41–7.27(m, 5H), 6.47(d, J=8.9Hz, 1H), 6.00(ddd, J=1.7, 2.3, 5.5Hz, 1H), 5.78(d, J=5.6Hz, 1H), 4.90(s, 1H), 4.51(d, J=11.2Hz, 1H), 4.45(d, J=11.2Hz, 1H), 4.04(d, J=8.2Hz, 1H), 3.76(d, J=2.3Hz, 1H), 2.85(dt, J=10.2, 8.2Hz, 1H), 2.49(ddd, J=2.3, 10.2, 15.8Hz, 1H), 2.23(ddd, J=1.7, 8.2, 15.8Hz, 1H), 1.40(s, 3H), 1.33(s, 3H). |
| 22 | CN | Bn | 7.65–7.16(m, 7H), 6.49(d, J=8.3Hz, 1H), 5.91(ddd, J=1.7, 2.3, 5.6Hz, 1H), 5.76(dd, J=2.3, 5.6Hz, 1H), 4.60(s, 1H), 4.50(d, J=11.2Hz, 1H), 4.44(d, J=11.2Hz, 1H), 3.99(d, J=8.3Hz, 1H), 3.70(d, J=2.3Hz, 1H), 2.83(dt, J=9.9, 8.3Hz, 1H), 2.50(ddd, J=2.3, 9.9, 14.2Hz, 1H), 2.20(ddd, J=1.7, 8.3, 14.2Hz, 1H), 1.39(s, 3H), 1.32(s, 3H). |

TABLE 3

| Ex. No. | R¹ | R¹⁴ | R¹⁵ | Z | R³ | ¹H-NMR (CDCl₃) δ: |
|---|---|---|---|---|---|---|
| 23 | NO₂ | Me | Me | OCO | Me | (CDCl₃): 7.88(s, 1H), 7.86(d, J=9.2Hz, 1H), 6.49(d, J=9.2Hz, 1H), 5.69(d, J=5.5Hz, 1H), 5.77(d, J=5.6Hz, 1H), 4.12(d, J=11.2Hz, 1H), 4.00(d, J=8.3Hz, 1H), 3.87(d, J=11.2Hz, 1H), 3.50(d, J=2.3Hz, 1H), 2.89(dt, J=9.9, 8.3Hz, 1H), 2.47(dd, J=9.9, 15.8Hz, 1H), 2.27(dd, J=8.8, 15.8Hz, 1H), 2.01(s, 3H), 1.09(s, 3H), 1.08(s, 3H). |
| 24 | NO₂ | H | H | NHCOO | Buᵗ | 7.71–7.66(m, 2H), 6.35(d, J=9.6Hz, 1H), 5.70–5.68(m, 1H), 5.56–5.54(m, 1H), 3.79(d, J=7.3Hz, 1H), 3.49–3.34(m, 2H), 3.07–2.97(m, 1H), 2.68–2.59(m, 1H), 2.26–2.13(m, 1H), 1.58(s, 9H), 1.56–1.46(m, 2H). |
| 25 | NO₂ | Me | Me | NHCOO | Buᵗ | 7.86–7.82(m, 2H), 6.58(d, J=8.6Hz, 1H), 5.96–5.94(m, 1H), 5.77–5.74(m, 1H), 4.84(brs, 1H), 4.70(m, 1H), 3.98(d, J=8.6Hz, 1H), 3.46–3.34(m, 2H), 2.92–2.84(m, 2H), 2.54–2.44(m, 1H), 2.31–2.23(m, 1H), 1.34(s, 9H), 1.03(s, 3H), 0.99(s, 3H). |
| 26 | CN | Me | Me | NHCOO | Buᵗ | 7.19(s, 1H), 7.17(d, J=7.9Hz, 1H), 6.64(d, J=7.9Hz, 1H), 5.88–5.85(m, 1H), 5.76–5.74(m, 1H), 4.69(brs, 1H), 3.98(d, J=7.9Hz, 1H), 3.42–3.38(m, 1H), 3.27(brs, 1H), 2.92–2.81(m, 2H), 2.55–2.45(m, 1H), 2.30–2.21(m, 1H), 1.35(s, 9H), 1.01(s, 3H), 0.99(s, 3H). |
| 27 | NO₂ | H | H | S | Me | 7.90(s, 1H), 7.85(dd, J=2.3, 8.9Hz, 1H), 6.64(d, J=8.9Hz, 1H), 5.90(brs, 1H), 5.79(brs, 1H), 4.00(d, J=8.6Hz, 1H), 3.66(dt, J=3.3, 6.6Hz, 1H), 2.86(ddd, J=3.3, 8.6, 17.0Hz, 1H), 2.77–2.57(m, 2H), 2.58–2.39(m, 1H), 2.28(dd, J=8.6, 17.0Hz, 1H), 2.17(s, 3H), 1.91–1.81(m, 2H). |
| 28 | NO₂ | Me | Me | S | Ph | 7.87–7.81(m, 3H), 7.39–7.35(m, 2H), 7.30–7.18(m, 2H), 6.42(d, J=8.9Hz, 1H), 5.96(brs, 1H), 5.77(brs, 1H), 4.48(brs, 1H), 3.99(d, J=8.9Hz, 1H), 3.63(brs, 1H), 3.10(d, J=12.5Hz, 1H), 3.03(d, J=12.5Hz, 1H), 3.01–2.91(m, 1H), 2.52–2.40(m, 1H), 2.30–2.20(m, 1H), 1.17(s, 6H). |

TABLE 3-continued

![structure with R1, R14, R15, Z, R3]

| Ex. No. | R¹ | R¹⁴ | R¹⁵ | Z | R³ | ¹H-NMR (CDCl₃) δ: |
|---|---|---|---|---|---|---|
| 29 | NO₂ | Me | Me | single bond | Cl | 7.88–7.84(m, 2H), 6.54(d, J=8.6Hz, 1H), 5.97(brs, 1H), 5.77(brs, 1H), 4.43 (brs, 1H), 4.02(d, J=7.9Hz, 1H), 3.64 (d, J=2.3Hz, 1H), 3.56(d, J=11.0Hz, 1H), 2.52(d, J= 11.0Hz, 1H), 2.93 (q, J=8.3Hz, 1H), 2.47(ddd, J=2.3, 10.0, 15.0Hz, 1H), 2.25(dd, J=6.6, 8.3Hz, 1H), 1.18(s, 3H), 1.14(s, 3H). |
| 30 | NO₂ | Me | Me | single bond | Br | 7.88–7.85(m, 2H), 6.55(d, J=8.9Hz, 1H), 5.97(brs, 1H), 5.77(brs, 1H), 4.33 (brs, 1H), 4.03(d, J=7.6Hz, 1H), 3.64 (brs, 1H), 3.52–3.43(m, 2H), 2.95 (dd, J=7.9, 17.5Hz, 1H), 2.52–2.43(m, 1H), 2.26(dd, J= 4.9, 14.5Hz, 1H), 1.21(s, 3H), 1.18(s, 3H). |

TABLE 4

![structure with O2N, i, R3]

| Ex. No. | i | R³ | ¹H-NMR (CDCl₃) δ: |
|---|---|---|---|
| 31 | 0 | Me | 8.22(d, J=2.6Hz, 1H), 7.90(dd, J=2.6, 9.2Hz, 1H), 6.42(d, J=9.2Hz, 1H), 5.99(brs, 1H), 5.13(d, J=7.3Hz, 1H), 3.94–3.74(m, 2H), 3.60(d, J=2.3Hz, 1H), 3.39(s, 3H), 3.36(d, J=9.2Hz, 1H), 3.16(d, J=9.2Hz, 1H), 2.16 (q, J=9.6Hz, 1H), 1.96–1.87(m, 2H), 1.11(s, 3H), 0.96 (s, 3H). |
| 32 | 0 | Bn | 8.21(d, J=2.3Hz, 1H), 7.87(dd, J=2.3, 8.9Hz, 1H), 7.43–7.30(m, 5H), 6.22(d, J=8.9Hz, 1H), 6.10(brs, 1H), 5.11(d, J=7.3Hz, 1H), 4.53(s, 2H), 3.88(q, J= 7.9Hz, 1H), 3.77(q, J=6.9Hz, 1H), 3.61(d, J=2.3Hz, 1H), 3.46(d, J=8.9Hz, 1H), 3.33(d, J=8.9Hz, 1H), 2.61(q, J=7.3Hz, 1H), 1.95–1.86(m, 2H), 1.14(s, 3H), 0.97(s, 3H). |

TABLE 4-continued

| Ex. No. | i | R³ | ¹H-NMR (CDCl₃) δ: |
|---|---|---|---|
| 33 | 1 | Me | 8.23(d, J=2.6Hz, 1H), 7.94(dd, J=2.6, 8.9Hz, 1H), 6.43(d, J=8.9Hz, 1H), 5.89(brs, 1H), 5.01(d, J=5.6Hz, 1H), 3.66–3.60(m, 1H), 3.49–3.34(m, 1H), 3.37(s, 3H), 3.32(d, J=8.9Hz, 1H), 3.17(d, J=8.9Hz, 1H), 2.27–2.24(m, 1H), 1.84–1.49(m, 5H), 1.13(s, 3H), 0.98(s, 3H). |
| 34 | 1 | Bn | 8.25–8.23(m, 1H), 7.90(dd, J=2.3, 8.9Hz, 1H), 7.45–7.31(m, 5H), 6.20(d, J=8.9Hz, 1H), 5.01(d, J=5.3Hz, 1H), 4.90(d, J=5.3Hz, 1H), 4.59(d, J=11.9Hz, 1H), 4.51(s, 1H), 4.44(d, J=11.9Hz, 1H), 3.66–3.62(m, 1H), 3.49–3.30(m, 2H), 3.29–3.16(m, 2H), 2.28–2.05(m, 1H), 1.80–1.34(m, 3H), 1.16(s, 3H), 0.98(s, 3H). |

EXAMPLE 35

Production of 4-(2-Hydroxy-1,1'-dimethyl-ethyl)-3a,4,5,9b-tetrahydro-3H-cyclopenta[c]quinoline-8-carbonitrile

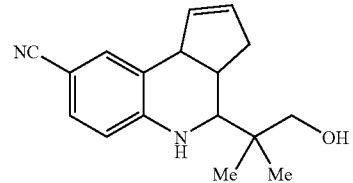

The compound of Example 3 (6.75 g) was dissolved in 60 ml of tetrahydrofuran, and 20 ml of a 1M tetrahydrofuran solution of tetrabutylammonium fluoride was added at 0° C. After 1 hour stirring at 0° C., the reaction mixture was concentrated under reduced pressure. The residue was purified by silica gel column chromatography (elution solvent: hexane:ethyl acetate=2:1) to obtain 3.6 g of the captioned compound. Its physical properties are shown below.

¹H-NMR (CDCl₃) δ: 7.19 (s, 1H), 7.17 (d, J=7.9 Hz, 1H), 6.50 (d, J=7.9 Hz, 1H), 5.87 (brs, 1H), 5.77 (brs, 1H), 3.93 (d, J=8.2 Hz, 1H), 3.60 (d, J=10.6 Hz, 1H), 3.53 (d, J=10.6 Hz, 1H), 3.47 (brs, 1H), 2.86 (dt, J=9.9, 8.2 Hz, 1H), 2.50 (dd, J=9.9, 15.8 Hz, 1H), 2.25 (dd, J=8.2, 15.8 Hz, 1H), 1.09 (s, 3H), 0.96 (s, 3H).

Compounds shown in Examples 36 to 39 were synthesized by using similar method of Example 35. The physical properties of the resulting compounds are shown in Tables 5 and 6.

TABLE 5

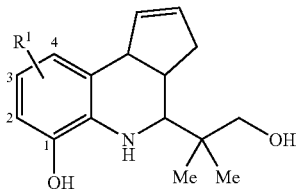

| Ex. No. | R[1] | $^1$H-NMR δ: |
|---|---|---|
| 36 | 2-NO$_2$ | (CDCl$_3$): 7.37(d, J=8.9Hz, 1H), 6.45(d, J=8.9Hz, 1H), 5.68(brs, 1H), 4.80(d, J=8.9Hz, 1H), 3.61(d, J=10.9Hz, 1H), 3.49(d, J=10.9Hz, 1H), 3.30(brs, 1H), 2.98(q, J=8.3Hz, 1H), 2.62–2.50(m, 1H), 2.25(dd, J=8.3, 15.2Hz, 1H), 1.05(s, 3H), 1.03(s, 3H). |
| 37 | 3-NO$_2$ | (DMSO-d$_6$): 10.12(s, 1H), 7.45(s, 1H), 7.32(s, 1H), 6.45(s, 1H), 5.99(brs, 1H), 5.71(d, J=5.3Hz, 1H), 5.25(t, J=4.6Hz, 1H), 3.96(d, J=7.9Hz, 1H), 3.44(s, 1H), 3.44–3.28(m, 2H), 2.81(q, J=8.6Hz, 1H), 2.60–2.45(m, 1H), 2.39–2.19(m, 1H), 1.03(s, 3H), 0.89(s, 3H). |

TABLE 6

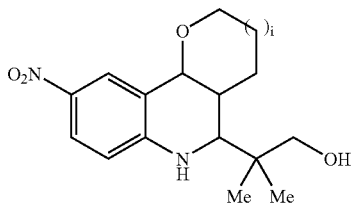

| Ex. No. | i | $^1$H-NMR (CDCl$_3$) δ: |
|---|---|---|
| 38 | 0 | 8.22(d, J=2.6Hz, 1H), 7.80(dd, J=2.3, 8.9Hz, 1H), 6.45(d, J=8.9Hz, 1H), 6.02(brs, 1H), 5.13(d, J=7.3Hz, 1H), 3.90(q, J=8.3Hz, 1H), 3.79(q, J=7.3Hz, 1H), 3.65(d, J=10.3Hz, 1H), 3.64(d, J=2.3Hz, 1H), 3.56(d, J=10.3Hz, 1H), 2.64(q, J=9.6Hz, 1H), 2.17–1.90(m, 2H), 1.13(s, 3H), 0.97(s, 3H). |
| 39 | 1 | 8.23(d, J=2.6Hz, 1H), 7.93(dd, J=2.6, 9.2Hz, 1H), 6.43(d, J=9.2Hz, 1H), 5.92(brs, 1H), 5.02(d, J=5.3Hz, 1H), 3.67–3.43(m, 3H), 2.30–2.26(m, 2H), 1.85–1.49(m, 5H), 1.15(s, 3H), 0.99(s, 3H). |

EXAMPLE 40

Production of acetic acid 2-(8-cyano-3a,4,5,9b-tetrahydro-3H-cyclopenta[c]quinolin-4-yl)-2-methylpropyl ester

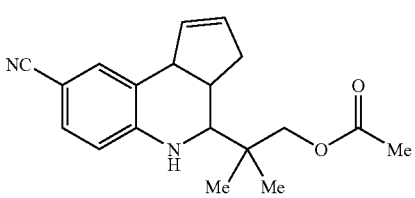

The compound of Example 35 (1.74 g) was dissolved in 20 ml of pyridine, and 5 ml of acetic anhydride was added at 0° C. After 12 hours stirring at room temperature, the reaction mixture was concentrated under reduced pressure. The residue was purified by silica gel column chromatography (elution solvent: hexane:ethyl acetate 4:1) to obtain 1.1 g of the captioned compound. Its physical properties are shown below.

$^1$H-NMR (CDCl$_3$) δ: 7.21 (s, 1H), 7.20 (d, J=8.3 Hz, 1H), 6.52 (d, J=8.3 Hz, 1H), 5.87 (brs, 1H), 5.77 (brs, 1H), 4.38 (s, 1H), 4.10 (d, J=11.2 Hz. 1H), 3.95 (d, J=7.9 Hz, 1H), 3.86 (d, J=11.2 Hz, 1H), 3.43 (brs, 1H), 2.87 (d, J=7.6 Hz, 1H), 2.49 (dd, J=9.9, 15.2 Hz, 1H), 2.25 (dd, J=7.6, 15.2 Hz, 1H), 2.11 (s, 3H), 1.07 (s, 6H).

Compounds shown in Examples 41 to 48 were synthesized by using similar method of Example 40. The physical properties of the resulting compounds are shown in Table 7.

TABLE 7

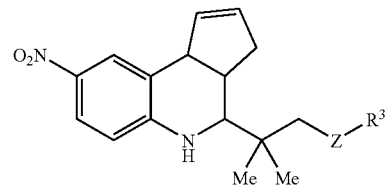

| Ex. No. | Z | R[3] | $^1$H-NMR (CDCl$_3$) δ: |
|---|---|---|---|
| 41 | OCO | Et | 7.88(s, 1H), 7.86(d, J=8.6Hz, 1H), 6.49(d, J=8.6Hz, 1H), 5.96(brs, 1H), 5.78(brs, 1H), 4.73(s, 1H), 4.14(d, J=11.2Hz, 1H), 4.00(d, J=7.9Hz, 1H), 3.87(d, J=11.2Hz, 1H), 3.49(brs, 1H), 2.89(q, J=7.9Hz, 1H), 2.53–2.47(m, 1H), 2.41(q, J=7.6Hz, 1H), 2.28(dd, J=7.9, 14.2Hz, 1H), 1.18(t, J=7.6Hz, 3H), 1.09(s, 6H). |
| 42 | OCO | Pr$^i$ | 7.88(s, 1H), 7.87(d, J=7.9Hz, 1H), 6.48(d, J=7.9Hz, 1H), 5.96(dd, J=3.0, 4.3Hz, 1H), 5.77(d, J=4.3Hz, 1H), 4.75(s, 1H), 4.14(d, J=11.2Hz, 1H), 4.00(d, J=8.3Hz, 1H), 3.86(d, J=11.2Hz, 1H), 3.50(d, J=1.7Hz, 1H), 2.89(q, J=8.3Hz, 1H), 2.62(q, J=6.9Hz, 1H), 2.49(dd, J=8.3, 15.5Hz, 1H), 2.28(dd, J=8.3, 15.5Hz, 1H), 1.22(d, J=6.9Hz, 3H), 1.21(d, J=6.9Hz, 3H), 1.09(s, 6H). |
| 43 | OCO | Bu$^a$ | 7.88(s, 1H), 7.86(d, J=8.9Hz, 1H), 6.49(d, J=8.9Hz, 1H), 5.95(brs, 1H), 5.78(brs, 1H), 4.73(s, 1H), 4.14(d, J=11.6Hz, 1H), 3.99(d, J=9.6Hz, 1H), 3.86(d, J=11.2Hz, 1H), 3.49(d, J=2.3Hz, 1H), 2.89(q, J=9.6Hz, 1H), 2.47(dd, J=9.6, 15.2Hz, 1H), 2.37(t, J=7.3Hz, 1H), 2.27(dd, J=9.6, 15.2Hz, 2H), 1.69–1.60(m, 2H), 1.47–1.16(m, 2H), 1.08(s, 6H), 0.92(t, J=7.3Hz, 3H). |
| 44 | OCO | Bu$^t$ | 7.88(s, 1H), 7.86(d, J=9.2Hz, 1H), 6.49(d, J=9.2Hz, 1H), 5.95(brs, 1H), 5.77(brs, 1H), 4.67(s, 1H), 4.13(d, J=11.6Hz, 1H), 3.99(d, J=8.6Hz, 1H), 3.84(d, J=11.6Hz, 1H), 3.49(brs, 1H), 2.89(dt, J=9.9, 8.6Hz, 1H), 2.47(dd, J=9.9, 15.2Hz, 1H), 2.27(dd, J=8.6, 15.2Hz, 1H), 1.25(s, 9H), 1.09(s, 6H). |
| 45 | OCO | Ph | 8.02(d, J=7.3Hz, 2H), 7.87(s, 1H), 7.84(dd, J=2.6, 8.9Hz, 1H), 7.62(t, J=7.3Hz, 2H), 7.59–7.45(m, 2H), 6.43(d, J=8.9Hz, 1H), 5.96(d, J=2.0Hz, 1H), 5.79(brs, 1H), 4.75(s, 1H), 4.36(d, J=11.2Hz, 1H), 4.17(d, J=11.2Hz, 1H), 4.01(d, J=8.3Hz, 1H), 3.60(d, J=2.3Hz, 1H), 2.95(q, J=8.3Hz, 1H), 2.51(dd, J=8.3, 15.2Hz, 1H), 2.31(dd, J=8.3, 15.2Hz, 1H), 1.20(s, 3H), 1.18(s, 3H). |
| 46 | OCO | 4-F-Ph | 8.05(dd, J=5.3, 8.6Hz, 2H), 7.87(s, 1H), 7.84(d, J=8.9Hz, 1H), 7.16(t, J=8.6Hz, 2H), 6.45(d, J=8.9Hz, 1H), 5.96(brs, 1H), 5.79(brs, 1H), 4.63(s, 1H), 4.35(d, J=11.2Hz, 1H), 4.16(d, J=11.2Hz, 1H), 4.00(d, J=8.6Hz, 1H), 3.58(d, J=2.0Hz, 1H), 2.95(q, J=8.6Hz, 1H), 2.51(dd, J=8.6, 13.2Hz, 1H), 2.32(dd, J=8.6, 13.2Hz, 1H), 1.19(s, 3H), 1.18(s, 3H). |

TABLE 7-continued

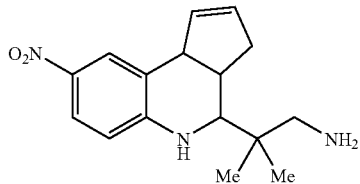

| Ex. No. | Z | R[3] | $^1$H-NMR (CDCl$_3$) δ: |
|---|---|---|---|
| 47 | OSO$_2$ | Et | 7.89(s, 1H), 7.87(d, J=7.6Hz, 1H), 6.54(d, J=7.6Hz, 1H), 5.97(ddd, J=2.3, 3.0, 5.6Hz, 1H), 5.78(brs, 1H), 4.55(s, 1H), 4.18(d, J=10.2Hz, 1H), 4.07(d, J=10.2Hz, 1H), 4.02(d, J=7.9Hz, 1H), 3.56(d, J=2.3Hz, 1H), 3.18(q, J=7.3Hz, 1H), 2.91(dq, J=2.3, 7.9Hz, 1H), 2.49(ddd, J=2.3, 7.9, 13.9Hz, 1H), 2.27(ddd, J=3.0, 7.9, 13.9Hz, 1H), 1.44(t, J=7.3Hz, 3H), 1.16(s, 3H), 1.12(s, 3H). |
| 48 | OSO$_2$ | 4-F-Ph | 7.93(dd, J=5.0, 8.9Hz, 2H), 7.89–7.85(m, 2H), 7.24(t, J=8.9Hz, 2H), 6.49(d, J=9.6Hz, 1H), 5.94(dt, J=1.7, 2.6Hz, 1H), 5.73(d, J=2.6Hz, 1H), 4.48(s, 1H), 3.96(d, J=8.3Hz, 1H), 3.93(d, J=9.9Hz, 1H), 3.89(d, J=9.9Hz, 1H), 3.47(d, J=2.0Hz, 1H), 2.80(dt, J=10.9, 8.3Hz, 1H), 2.39(ddd, J=2.6, 8.3, 15.5Hz, 1H), 2.17(ddd, J=1.7, 10.9, 15.5Hz, 1H), 1.07(s, 3H), 1.05(s, 3H). |

EXAMPLE 49

Production of 2-methyl-2-(8-nitro-3a,4,5,9b-tetrahydro-3H-cyclopenta[c]quinolin-4-yl)-propylamine

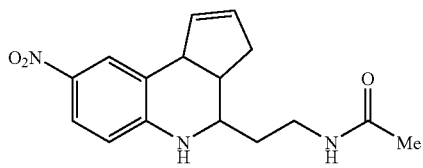

The compound of Example 25 (200 mg) was dissolved in 5 ml of ethyl acetate, and 1 ml of a 4N hydrochloric acid-ethyl acetate solution was added. After overnight stirring at room temperature, the reaction mixture was concentrated under reduced pressure. The residue was purified by silica gel column chromatography (elution solvent: ethyl acetate:methanol=2:1) to obtain 123 mg of the captioned compound. Its physical properties are shown below.

$^1$H-NMR (CDCl$_3$) δ: 8.01 (brs, 1H), 7.81–7.77 (m, 2H), 7.45 (s, 1H), 6.90 (d, J=9.9 Hz, 1H), 6.38 (brs, 1H), 5.97–5.95 (m, 1H), 5.74–5.72 (m, 1H), 4.00 (d, J=8.6 Hz, 1H), 3.52 (brs, 1H), 3.47 (dd, J=7.3, 14.2 Hz, 1H:), 2.47–2.37 (m, 1H), 2.27–2.22 (m, 1H), 1.24 (s, 3H), 1.17 (s, 3H).

EXAMPLE 50

Production of 2-(8-nitro-3a,4,5,9b-tetrahydro-3H-cyclopenta[c]quinolin-4-yl)-propylamine

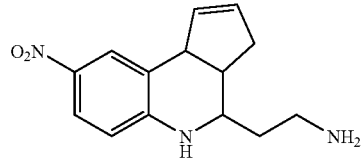

The similar method of Example 49 was performed using 65 mg of the compound of Example 24 to obtain 32 mg of the captioned compound. Its physical properties are shown below.

$^1$H-NMR (CDCl$_3$) δ: 7.90–7.85 (m, 2H), 6.54 (d, J=9.5 Hz, 1H), 5.89–5.87 (m, 1H), 5.75–5.73 (m, 1H), 3.9.8 (d, J=7.9 Hz, 1H), 3.68–3.53 (m, 1H), 3.26–3.16 (m, 1H), 2.87–2.78 (m, 1H), 2.45–2.32 (m, 2H), 1.75–1.65 (m, 2H).

EXAMPLE 51

Production of N-[2-(8-nitro-3a,4,5,9b-tetrahydro-3H-cyclopenta[c]quinolin-4-yl)-ethyl]-acetamide The compound of Example 50 (40 mg) and 0.04 ml of triethylamine were dissolved in 2 ml of dimethylformamlde, and 0.62 ml of acetic anhydride was added. After 2 hours stirring at room temperature, the reaction mixture was diluted with water and ethyl acetate. The ethyl acetate layer was washed with water, dried over anhydrous sodium sulfate, and concentrated under reduced pressure. The residue was purified by silica gel column chromatography (elution solvent: hexane:ethyl acetate 1:1) to obtain 36 mg of the captioned compound. Its physical properties are shown below.

$^1$H-NMR (CDCl$_3$) δ: 7.90 (s, 1H), 7.86 (d, J=6.9 Hz, 1H), 6.57 (d, J=8.9 Hz, 1H), 5.92–5.89 (m, 1H), 5.79–5.74 (m, 1H), 5.29 (brs, 1H), 3.95 (d, J=7.9 Hz, 1H), 3.63–3.44 (m, 2H), 3.35–3.23 (m, 1H), 2.84–2.78 (m, 1H), 2.46–2.,28 (m, 2H), 2.01 (s, 3H).

Compounds shown in Examples 52 to 63 were synthesized by using similar method of Example 51. The physical properties of the resulting compounds are shown in Table 8.

TABLE 8

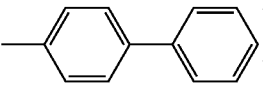

| Ex. No. | Z | R³ | ¹H-NMR (CDCl₃) δ: |
|---|---|---|---|
| 52 | NHCO | Me | 7.85(s, 1H), 7.83(d, J=9.9Hz, 1H), 6.63(d, J=9.9Hz, 1H), 6.22(brs, 1H), 5.82–5.80(m, 1H), 5.78–5.75(m, 1H), 5.10(brs, 1H), 3.95(d, J=8.3Hz, 1H), 3.62(dd, J=7.9, 14.2Hz, 1H), 3.30(m, 1H), 2.93–2.81(m, 1H), 2.52–2.42(m, 1H), 2.31–2.28(m, 1H), 1.97(s, 3H), 1.06(s, 3H), 1.01(s, 3H). |
| 53 | NHCO | Pr$^i$ | 7.86(s, 1H), 7.83(d, J=9.9Hz, 1H), 6.62(d, J=9.9Hz, 1H), 5.96–5.94(m, 1H), 5.78–5.76(m, 1H), 5.65(brs, 1H), 4.97(brs, 1H), 3.96(d, J=8.3Hz, 1H), 3.69(dd, J=8.3, 14.5Hz, 1H), 3.24(d, J=2.0Hz, 1H), 2.93–2.82(m, 3H), 2.54–2.44(m, 1H), 2.38–2.27(m, 1H), 1.10(d, J=8.3Hz, 3H), 1.05(d, J=8.3Hz, 3H), 1.02(s, 3H), 1.01(s, 3H). |
| 54 | NHCO | CH₂CHMe₂ | 7.86(s, 1H), 7.84(d, J=9.6Hz, 1H), 6.63(d, J=9.6Hz, 1H), 5.97–5.96(m, 1H), 5.95–5.94(m, 1H), 5.64(brs, 1H), 4.97(brs, 1H), 3.95(d, J=8.3Hz, 1H), 3.69(dd, J=8.3, 14.2Hz, 1H), 3.24(brs, 1H), 2.89(dd, J=5.3, 14.5Hz, 2H), 2.53–2.44(m, 1H), 2.38–2.30(m, 1H), 1.12(s, 3H), 1.10(s, 3H), 1.05(d, J=7.9Hz, 3H), 1.04(d, J=7.9Hz, 3H). |
| 55 | NHCO | Bu$^t$ | 7.85(s, 1H), 7.83(d, J=9.9Hz, 1H), 6.65(d, J=9.9Hz, 1H), 6.10–6.06(m, 1H), 5.97–5.95(m, 1H). 5.77–5.75(m, 1H), 5.16(brs, 1H), 3.95(d, J=7.9Hz, 1H), 3.65(dd, J=8.25, 14.5Hz, 1H), 3.22(d, J=2.31Hz, 1H), 2.96–2.82(m, 2H), 2.54–2.49(m, 2H), 2.36–2.28(m, 2H), 1.13(s, 3H), 1.07(s, 3H), 1.02(s, 3H). |
| 56 | NHCO | Ph | 7.86–7.83(m, 2H), 7.75(d, J=8.3Hz, 2H), 7.51–7.38(m, 3H), 7.12(brs, 1H), 6.70(d, J=9.2Hz, 1H), 5.98–5.95(m, 1H), 5.79–5.77(m, 1H), 5.35(brs, 1H), 3.94(d, J=6.9Hz, 1H), 3.78(dd, J=7.9, 14.2Hz, 1H), 3.39(s, 1H), 3.20(dd, J=5.6, 14.2Hz, 1H), 2.51–2.43(m, 1H), 2.34–2.25(m, 1H), 1.15(s, 3H), 1.09(s, 3H). |
| 57 | NHCO | biphenyl | 7.89–7.77(m, 4H), 7.65–7.57(m, 4H), 7.49–7.36(m, 3H), 6.68(d, J=8.9Hz, 1H), 6.42–6.38(m, 1H), 5.97(brs, 1H), 5.79(brs, 1H), 5.06(m, 1H), 3.95(d, J=7.6Hz, 1H), 3.87(dd, J=8.3, 14.5Hz, 1H) 3.38(d, J=2.3Hz, 1H), 3.19(dd, J=5.6, 14.5Hz, 1H), 2.92–2.86(m, 1H), 2.56–2.48(m, 1H), 2.36–2.27(m, 1H), 1.16(s, 3H), 1.11(s, 3H). |
| 58 | NHCOCO | OEt | 7.86(s, 1H), 7.84(d, J=6.9Hz, 1H), 7.83(brs, 1H), 6.62(d, J=6.9Hz, 1H), 6.00–5.98(m, 1H), 5.97–5.95(m, 1H), 4.64(brs, 1H), 4.39(q, J=7.3Hz, 2H), 3.96(d, J=7.6Hz, 1H), 3.60(dd, J=7.9, 14.2Hz, 1H), 2.96–2.84(m, 1H), 2.52–2.43(m, 1H), 2.33–2.24(m, 1H), 1.38(t, J=7.3Hz, 3H), 1.11(s, 3H), 1.08(s, 3H). |
| 59 | NHSO₂ | Me | 7.74(s, 1H), 7.70(d, J=8.9Hz, 1H), 6.45(d, J=8.9Hz, 1H), 5.58–5.67(m, 1H), 5.68–5.65(m, 1H), 4.76(t, J=6.9Hz, 1H), 4.57(brs, 1H), 3.88(d, J=7.9Hz, 1H), 3.42(d, J=1.7Hz, 1H), 3.09(dd, J=6.9, 13.5Hz, 1H), 2.95(dd, J=7.3, 13.5Hz, 1H), 2.87(s, 3H), 2.86–2.75(m, 1H), 2.41–2.36(m, 1H), 2.22–2.13(m, 1H), 1.00(s, 3H), 0.97(s, 3H). |
| 60 | NHSO₂ | Et | 7.84(s, 1H), 7.80(d, J=8.2Hz, 1H), 6.64(d, J=8.2Hz, 1H), 6.62–6.52(m, 1H), 5.96(brs, 1H), 5.76(brs, 1H), 5.20(brs, 1H), 3.99–3.96(m, 1H), 3.55(brs, 1H), 3.51–2.87(m, 5H), 2.53–2.49(m, 1H), 2.28–2.18(m, 1H), 1.35(t, J=7.3Hz, 3H), 1.06(s, 3H), 1.03(s, 3H). |
| 61 | NHSO₂ | 4-F-Ph | 7.89–7.83(m, 4H), 7.22–7.16(m, 2H), 6.67(d, J=9.6Hz, 1H), 5.97–5.95(m, 1H), 5.75–5.73(m, 1H), 4.88(t, J=7.6Hz, 1H), 4.60(brs, 1H), 3.96(d, J=7.9Hz, 1H), 3.48(brs, 1H), 3.00–2.83(m, 2H), 2.44–2.34(m, 1H), 2.23–2.14(m, 1H), 1.06(s, 3H), 1.03(s, 3H). |
| 62 | NHSO₂ | 4-Cl-Ph | 7.87–7.80(m, 2H), 7.77(d, J=8.6Hz, 2H), 7.48(d, J=8.6Hz, 2H), 6.65(d, J=9.6Hz, 1H), 5.97–5.95(m, 1H), 5.75–5.73(m, 1H), 4.80(t, J=7.3Hz, 1H), 4.55(brs, 1H), 3.95(d, J=7.9Hz, 1H), 3.47(d, J=2.0Hz, 1H), 3.01–2.28(m, 3H), 2.24–2.35(m, 1H), 2.22–2.17(m, 1H), 1.06(s, 3H), 1.03(s, 3H). |

TABLE 8-continued

| Ex. No. | Z | R³ | ¹H-NMR (CDCl₃) δ: |
|---|---|---|---|
| 63 | NHSO₂ | 4-AcNH-Ph | 7.84–7.80(m, 2H), 7.75(d, J=8.6Hz, 2H), 7.58(d, J= 8.6Hz, 2H), 6.52(d, J=9.6Hz, 1H), 5.93–5.91(m, 1H), 5.73–5.71(m, 1H), 5.00(t, J=7.3Hz, 1H), 4.63(s, 1H), 3.91(d, J=7.9Hz, 1H), 3.43(s, 1H), 2.88–2.80(m, 2H), 2.43–2.34(m, 1H), 2.22–2.13(m, 1H), 2.05(s, 3H), 1.03(s, 3H), 1.01(s, 3H). |

EXAMPLE 64

Production of 1-isopropyl-3-[2-methyl-2-(8-nitro-3a,4,5,9b-tetrahydro-3H-cyclopenta[c]quinolin-4-yl)-propyl]urea

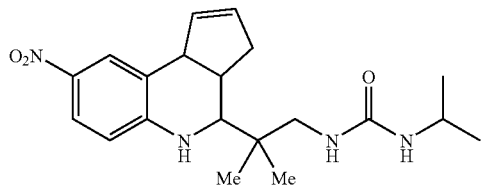

The compound of Example 49 (57 mg) was dissolved in 2 ml of dimethylformamide, and 0.03 ml of isopropyl isocyanate was added. After 30 minutes stirring at room temperature, the reaction mixture was diluted with water and ethyl acetate. The ethyl acetate layer was washed with water, dried over anhydrous sodium sulfate, and concentrated under reduced pressure. The residue was purified by silica gel column chromatography (elution solvent: hexane:ethyl acetate=1:1) to obtain 62 mg of the captioned compound. Its physical properties are shown below.

¹H-NMR (CDCl₃) δ: 7.84–7.80 (m, 2H), 6.60 (d, J=9.23 Hz, 1H), 5.96 (brs, 1H), 5.78 (brs, 1H), 5.20 (brs, 1H), 4.51–4.40 (m, 1H), 4.18–4.07 (m, 1H), 3.95 (d, J=7.3 Hz, 1H), 3.77 (brs, 1H), 3.56 (dd, J=7.9, 14.5 Hz, 1HI), 3.34 (s, 1H), 2.93–2.84 (m, 2H), 2.53–2.43 (m, 1H), 2.32–2.123 (m, 1H), 1.12 (s, 3H), 1.10 (s, 3H), 1.02 (d, J=5.9 Hz, 3H), 1.00 (d, J=5.9 Hz, 3H).

Compounds shown in Examples 65 to 72 were synthesized by using similar method of Example 64. The physical properties of the resulting compounds are shown in Table 9.

TABLE 9

| Ex. No. | Z | R³ | ¹H-NMR (CDCl₃) δ: |
|---|---|---|---|
| 65 | NHCONH | 3-Me-Ph | 7.83–7.79(m, 2H), 7.23–7.17(m, 3H), 7.04–6.87(m, 2H), 6.57(d, J=8.3Hz, 1H), 6.32(brs, 1H), 5.98–5.96(m, 1H), 5.80–5.78(m, 1H), 5.02–5.01(m, 2H), 3.95(d, J=7.6Hz, 1H), 3.58(dd, J=7.6, 14.2Hz, 1H), 3.37(d, J=1.3Hz, 1H), 3.00(dd, J=5.6, 14.5Hz, 1H), 2.89–2.82(m, 1H), 2.53–2.43(m, 1H), 2.30–2.24(m, 1H), 2.30(s, 3H), 1.03(s, 3H), 1.01(s, 3H). |
| 66 | NHCONH | 4-NO₂-Ph | 8.23(t, J=2.0Hz, 1H), 7.85–7.77 (m, 2H), 7.71(d, J=2.3Hz, 1H), 7.62(dd, J=2.6, 9.2Hz, 1H), 7.48–7.37(m, 2H), 6.46(d, J=8.9Hz, 1H), 5.94–5.92(m, 1H), 5.81–5.79(m, 1H), 5.73(t, J=5.9Hz, 1H), 4.86(brs, 1H), 3.93(d, J=6.9Hz, 1H), 3.49–3.41(m, 2H), 3.27(dd, J=7.3, 14.8Hz, 1H), 2.94–2.87(m, 1H), 2.55–2.47(m, 1H), 2.37–2.28(m, 1H), 1.12(s, 3H), 1.06(s, 3H). |
| 67 | NHCSNH | Me | 7.86(s, 1H), 7.82(d, J=9.6Hz, 1H), 6.63(d, J=9.6Hz, 1H), 6.01–5.99 (m, 1H), 5.79–5.77(m, 1H), 5.19 (brs, 1H), 4.30(dd, J=8.2, 14.2Hz, 1H), 3.94(d, J=8.6Hz, 1H), 3.33(d, J=2.3Hz, 1H), 3.22(dd, J=4.6, 14.5Hz, 1H), 2.94(d, J=5.3Hz, 3H), 1.13(s, 3H), 1.07(s, 3H). |
| 68 | NHCSNH | Et | 7.86(s, 1H), 7.83(d, J=9.6Hz, 1H), 6.63(d, J=9.6Hz, 1H), 5.99(brs, 1H), 5.89(brs, 1H), 5.79–5.70(m, 2H), 5.21(brs, 1H), 4.34–4.26(m, 1H), 3.94(d, J=7.6Hz, 1H), 3.32 (q, J=7.3Hz, 2H), 3.24(dd, J= 5.0, 14.5Hz, 1H), 2.88–2.82(m, 1H), 2.53–2.44(m, 1H), 2.33–2.24(m, 1H), 1.22(t, J=7.3Hz, 3H), 1.13(s, 3H), 1.06(s, 3H). |

TABLE 9-continued

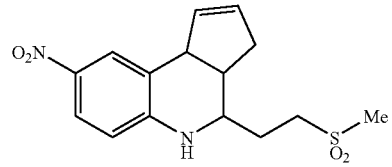

| Ex. No. | Z | R³ | ¹H-NMR (CDCl₃) δ: |
|---|---|---|---|
| 69 | NHCSNH | Pr^i | 7.83(s, 1H), 7.82(d, J=9.0Hz, 1H), 6.44(d, J=9.0Hz, 1H), 5.98–5.97 (m, 3H), 5.25(brs, 1H), 4.28–4.08 (m, 2H), 3.93(d, J=835Hz, 1H), 3.34(brs, 1H), 3.23(dd, J=5.0, 14.5Hz, 1H), 2.88–2.81(m, 1H), 2.52–2.42(m, 1H), 2.33–2.27 (m, 1H), 1.19(d, J=6.6Hz, 3H), 1.17(d, J=6.6Hz, 3H), 1.12(s, 3H), 1.06(s, 3H). |
| 70 | NHCSNH | cyclohexylmethyl | 7.88–7.83(m, 2H), 6.64(d, J=9.6Hz, 1H), 6.02–5.98(m, 1H), 5.79–5.77(m, 1H), 5.68–5.63 (m, 1H), 5.20(brs, 1H), 4.26(dd, J=8.3, 14.2Hz, 1H), 3.95(d, J=9.6Hz, 1H), 3.65–3.54(m, 1H), 3.32(d, J=2.0Hz, 1H), 3.21 (dd, J=4.6, 14.2Hz, 1H), 2.89–2.78(m, 1H), 2.53–2.43(m, 1H), 2.33–2.24(m, 1H), 1.96–1.92(m, 2H), 1.76–1.68(m, 2H), 1.35–1.15(m, 6H), 1.12(s, 3H), 1.06(s, 3H). |
| 71 | NHCSNH | Ph | 7.86–7.82(m, 2H), 7.74(brs, 1H), 7.48–7.43(m, 2H), 7.35(d, J=7.6Hz, 1H), 7.17(d, J=7.6Hz, 2H), 6.68(d, J=8.6Hz, 1H), 6.17(brs, 1H), 5.99(brs, 1H), 5.78(brs, 1H), 5.07(brs, 1H), 4.29(dd, J=8.6, 14.5Hz, 1H), 3.90(d, J=7.3Hz, 1H), 3.27(m, 1H), 3.23(dd, J=4.6, 9.9Hz, 1H), 2.84–2.80(m, 1H), 2.50–2.42(m, 1H), 2.30–2.21(m, 1H), 1.03(s, 3H), 0.99(s, 3H). |
| 72 | NHCSNH | 4-Br-Ph | 8.01(brs, 1H), 7.86–7.82(m, 2H), 7.54(d, J=8.6Hz, 2H), 7.10(d, J=8.6Hz, 2H), 6.56(d, J=9.6Hz, 1H), 6.35–6.30(m, 1H), 6.00–5.98(m, 1H), 5.79–5.77(m, 1H), 5.00(brs, 1H), 4.25(dd, J=7.9, 14.2Hz, 1H), 3.50(d, J=7.9Hz, 1H), 3.32–3.24 (m, 2H), 2.84(q, J=8.2Hz, 1H), 2.28–2.41(m, 1H), 2.32–2.23(m, 1H), 1.04(s, 3H), 1.03(s, 3H). |

EXAMPLE 73, 74

Production of 4-(2-methanesulfinyl-ethyl)-8-nitro-3a,4,5,9b-tetrahydro-3H-cyclopenta[c]quinoline (Example 73) and 4-(2-methanesulfonyl-ethyl)-8-nitro-3a,4,5,9b-tetrahydro-3H-cyclopenta[c] quinoline (Example 74)

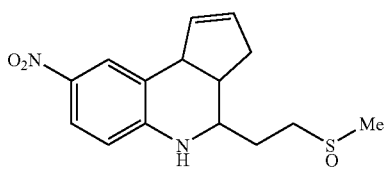

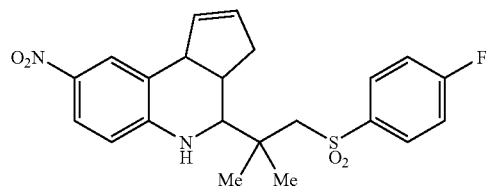

The compound of Example 27 (70.5 mg) was dissolved in 5 ml of dichloromethane, and 217 mg of m-chloroperbenzoic acid was added at 0° C. After 30 minutes stirring at room temperature, the reaction mixture was diluted with a saturated sodium hydrogen carbonate solution and ethyl acetate. The ethyl acetate layer was washed with a saturated sodium chloride solution, dried over anhydrous magnesium sulfate, and concentrated under reduced pressure. The residue was purified by silica gel column chromatography (elution solvents: hexane:ethyl acetate=1:2~ethyl acetate~ethyl acetate:methanol=9:1) to obtain 13.8 mg of the compound of Example 73 and 44 mg of the compound of Example 74. Their physical properties are shown below.

Example 73: ¹H-NMR (CDCl₃) δ: 8.07–7.80 (m, 2H), 6.53 (dd, J=1.3, 8.9 Hz, 1H), 5.89 (brs, 1H), 5.74 (brs, 1H), 4.00 (d, J=9.6 Hz, 1H), 3.66–3.56 (m, 1H), 2.99–2.80 (m, 3H), 2.68 (s,-3H×20/33), 2.64 (s, 3H×13/33).

Example 74: ¹H-NMR (CDCl₃) δ: 7.91 (s, 2H), 7.87 (d, J=8.6 Hz, 1H), 6.43 (d, J=8.6 Hz, 1H), 5.91 (brs, 1H), 5.76 (brs, 1H), 4.02 (d, J=9.2 Hz, 1H), 3.80–3.71 (m, 1H), 3.29–3.10 (m, 2H), 3.00 (s, 3H), 2.88 (ddd, J=2.6, 8.5, 16.2 Hz, 1H), 2.53–2.43 (m, 1H), 2.30 (dd, J=8.5, 16.2 Hz, 1H), 2.17–2.09 (m, 2H).

EXAMPLE 75

Production of 4-[2-(4-fluoro-benzenesulfonyl)-1,1'-dimethyl-ethyl]-8-nitro-3a,4,5,9b-tetrahydro-3H-cyclopenta[c]quinoline The captioned compound (16 mg) was obtained in the similar method of Example 73 with the use of 20 mg of the compound of Example 28, Its physical properties are shown below.

¹H-NMR (CDCl₃) δ: 7.88–7.83 (m, 2H), 7.31–7.21 (m, 2H), 6.80 (d, J=7.3 Hz, 1H), 6.73 (dd, J=3.3, 8.3 Hz, 1H), 6.59 (dd, J=3.6, 9.2 Hz, 1H), 6.42 (brs, 1H×1/2), 5.99–5.96 (m, 1H), 5.76 (brs, 1H), 5.49 (brs, 1H×1/2), 5.49 (brs, 1H×1/2), 3.99 (brs, 1H), 3.89 (d, J=13.9 Hz, 1H×1/2), 3.77 (d, J=14.2 Hz, 1H×1/2), 3.63 (d. J=2.0 Hz, 1H×1/2), 3.46 (d, J=2.0 Hz, 1H×1/2), 2.98–2.84 (m, 1H), 2.66 (d: J=14.2 Hz, 1H×1/2), 2.58 (d, J=13.9 Hz, 1H×1/2), 2.56.–2.44 (m, 1H), 2.30–2.15 (m, 1H), 1.45 (s, 3H×1/2), 1.40 (s, 3H×1/2), 1.29 (s, 6H×1/2).

EXAMPLE 76

Production of thioacetic acid S-[2-methyl-2-(8-nitro-3a,4,5,9b-tetrahydro-3H-cyclopenta[c]quinolin-4-yl) propyl]ester

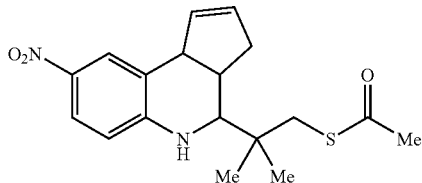

The compound of Example 30 (100 mg) and 40 μl of triethylamine were dissolved in 5 ml of dimethylformamide, and 98 mg of potassium thioacetate was added. After stirring for 20 minutes at room temperature, then for 6 hours and 30 minutes at 50° C., the reaction mixture was diluted with water and ethyl acetate. The ethyl acetate layer was washed with a saturated sodium chloride solution, dried over anhydrous magnesium sulfate, and concentrated under reduced pressure. The residue was purified by silica gel column chromatography (elution solvents: hexane:ethyl acetate= 20:1~10:1~9:1) to obtain 84 mg of the captioned compound. Its physical properties are shown below.

$^1$H-NMR (CDCl$_3$) δ: 7.87 (s, 1H), 7.86 (d, J=6.9 Hz, 1H), 6.57 (d, J=6.9 Hz, 1H), 5.99–5.94 (m, 1H), 5.79–5.75 (m, 1H), 4.47 (brs, 1H), 3.97 (d, J=8.3 Hz, 1H), 3.4:4 (d, J=2.0 Hz, 1H), 3.24 (d, J 4.2 Hz, 1H), 2.93–2.81 (m, 1H), 2.84 (d, J=4.2 Hz, 1H), 2.53–2.40 (m, 1H), 2.34 (s, 3H), 2.34–2.23 (m, 1H), 1.10 (s, 3H), 1.06 (s, 3H).

EXAMPLE 77

Production of 2-methyl-2-(8-nitro-3a,4,5,9b-tetrahydro-3H-cyclopenta[c]quinolin-4-yl)-propane-1-thiol

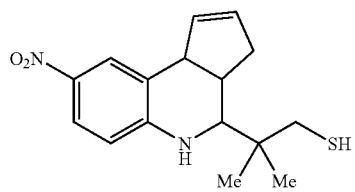

The compound of Example 76 (134 mg) was dissolved in 15 ml of a mixed solution of methanol and tetrahydrofuran, and 15 ml of a 2 mol/l sodium hydroxide solution was added. After overnight stirring at 50° C., the reaction mixture was concentrated under reduced pressure. The resulting residue was acidified with saturated ammonium chloride solution and 2 mol/l hydrochloric acid solution, and then ethyl acetate was added. The ethyl acetate layer was washed with a saturated sodium chloride solution, dried over anhydrous magnesium sulfate, and concentrated under reduced pressure. The residue was purified by silica gel column chromatography (elution solvents: hexane:ethyl acetate 4:1~hexane:ethyl acetate=2:1~hexane:ethyl acetate=1:1) to obtain 34 mg of the captioned compound. Its physical properties are shown below.

$^1$H-NMR (CDCl$_3$) δ: 7.88 (s, 1H), 7.88–7.83 (m, 1H), 6.52 (d, J=8.6 Hz, 1H), 5.96 (brs, 1H), 5.78 (brs, 1H), 4.39 (brs, 1H), 4.00 (brd, J=8.9 Hz, 1H), 3.53 (dd, J=1.7 Hz, 1H), 3.03–2.86 (m, 3H), 2.52–2.42 (m, 1H), 2.29:–2.20 (m, 1H), 1.14 (s, 3H), 1.07 (s, 3H).

Next, the usefulness of the compounds of the present invention will be described by the following test examples:

TEST EXAMPLE 1

Test for Competitive Binding to Rat Androgen Receptors (Rat AR)

Preparation of rat AR fraction: Prostates were harvested into ice-cooled ET buffer (10 mM Tris, 1 mM EDTA, 5 mM DTT, 10 mM sodium molybdate, pH 7.4) 3 days after orchiectomy in 11-week-old male SD rats. The prostate was finely cut, and ET buffer was added, whereafter the mixture was homogenized using a homogenizer. The homogenate was ultracentrifuged (100,000×g, 60 min, 4° C.), and the supernatant was used as a rat AR fraction (hereinafter referred to as ARF).

Binding test: $^3$H-testosterone (hereinafter referred to as $^3$H-T) was diluted with ET buffer. Dihydrotestosterone (DHT) was prepared so as to have a concentration (final concentration 1 μM) 400 times the maximum concentration of $^3$H-T (2.5 nM). The $^3$H-T solution was added to a 1.5 ml tube containing DHT, no DHT, or the test compound with a varying concentration. Further, 200 μg ARF was added to adjust the final volume to 100 μl. The mixture was incubated for 2 hours at 4° C., and then 300 μl of a 0.05% dextran T70-1.0% activated carbon solution was added. The mixture was further incubated for 15 minutes in ice to remove the free $^3$H-T. After centrifugation (4° C., 2,500 rpm, 5 min), 275 μl of the supernatant was harvested into a liquid scintillation vial, and 2 ml of clear-sol was added. The mixture was stirred, allowed to stand, and measured for $^3$H radioactivity with a liquid scintillation counter.

Calculation of the relative binding inhibition rate: The binding inhibition rate (%) of the compound according to the present invention was calculated from the following equation, and the 50% inhibition concentration (IC$_{50}$) was calculated by the probit analysis of the concentration-binding inhibition curve.

Binding inhibition rate (%)=100×[1−(a−c)/(b−c)]

where
a: Radioactivity of the sample incorporating the compound of the present invention ($^3$H-T+compound)
b: Radioactivity of the sample free from the compound of the present invention (only $^3$H-T: amount of total binding)
c: Radioactivity of the sample incorporating DHT ($^3$H-T+DHT: amount of nonspecific binding)

The relative binding inhibition rate (RBA: Relative Binding Affinity) was obtained from the following equation (Endocrinology 138, 863–870, 1997):

RBA=100×(IC$_{50}$ of hydroxyflutamide)/(IC$_{50}$ of the compound of the present invention)

RBA's of the compounds of the present invention, calculated as above, are shown in Table 10.

TABLE 10

| Test Compounds | RBA |
| --- | --- |
| Example 1 | 4751 |
| Example 7 | 65 |
| Example 19 | 57 |
| Example 21 | 74 |
| Example 29 | 75 |
| Example 35 | 236 |
| Example 39 | 829 |
| Example 40 | 96 |
| Example 52 | 478 |
| Example 53 | 55 |
| Example 59 | 2288 |
| Example 60 | 814 |
| Example 61 | 169 |
| Example 63 | 580 |
| Example 64 | 298 |
| Example 68 | 491 |
| Example 69 | 244 |
| Example 76 | 131 |
| Hydroxyflutamide | 100 |

The RBA's determined, with the binding inhibition rate of hydroxyflutamide taken as 100, showed the compounds of the present invention to have very strong binding inhibition activity.

TEST EXAMPLE 21

Action of Increasing Prostate Weight in Orchiectomized Rats

Testes were removed from 8- to 12-week-old male SD rats. From 5 days postoperation, the compound of the present invention (3, 30 mg/kg), suspended in a 0.5% methyl cellulose solution, was subcutaneously injected once daily for a consecutive week, and 6 days weekly for 8 consecutive weeks. On the next day after final administration, the wet weight of the ventral prostate was measured to evaluate the in vivo AR agonistic effect of the compound of the present invention. The results are shown in Tables 11 and 12.

TABLE 11

| Test compounds | Weight of prostate mg/body weight (100 g) |
| --- | --- |
| 1-week treatment | |
| Normal control (sham) | 100 ± 11 |
| Comp. example (Veh) | 8 ± 2 |
| Ex. 1 3 mg/kg | 18 ± 4** |
| Ex. 1 30 mg/kg | 26 ± 3** |

Mean ± SD
*$p < 0.05$,
**$p < 0.01$ on Dunnett's t-test.

TABLE 12

| Test compounds | Weight of prostate mg/body weight (100 g) |
| --- | --- |
| 8-week treatment | |
| Normal control (sham) | 104 ± 22 |
| Comp. example (Veh) | 8 ± 1 |

TABLE 12-continued

| Test compounds | Weight of prostate mg/body weight (100 g) |
| --- | --- |
| Ex. 1 3 mg/kg | 52 ± 8** |
| Ex. 1 30 mg/kg | 97 ± 14** |

Mean ± SD
*$p < 0.05$,
**$p < 0.01$ on Dunnett's t-test.

The compound of Example 1, when consecutively administered for 1 week, significantly increased prostate weights in comparison with the comparative example. When the duration of treatment was extended to 8 weeks, this compound restored the atrophied prostate up to the level of the normal control, demonstrating significant AR agonistic activity.

TEST EXAMPLE 3

Action of Increasing Prostate Weight in Rats After Orchiectomized (ORX) Rats

Orchiectomy was performed in 8-week-old male SD rats. From 5 days postoperation, the compound of the present invention (Example 60, 30 mg/kg), dissolved in a 5% dimethyl sulfoxide-containing olive oil solution, was subcutaneously injected once daily for 8 days. On the next day after final administration, the wet weight of the ventral prostate was measured to evaluate the AR agonistic effect of the compound of the present invention. The results are shown in Table 13.

TABLE 13

| | Weight of prostate (mg/body weight 100 g) |
| --- | --- |
| Normal control (Sham) | 103 ± 12 |
| ORX Comp. example (Vehicle) | 10 ± 1++ |
| Ex. 69 30 mg/kg | 21 ± 2** |

Mean ± SD
**$p < 0.01$ on Dunnett's t-test (vs Vehicle).
++$p < 0.01$ on unpaired t-test (vs Sham).

The compound of Example 60, when administered for 8 consecutive days, significantly increased the prostate weights in comparison with the comparative example, demonstrating excellent AR agonistic activity.

TEST EXAMPLE 4

Action of Increasing Prostate Weight and Bone Mineral Density in Orchiectomized (ORX) Rats Orchiectomy was performed in 12-week-old male SD rats. From the next day postoperation, the positive control compound dihydrotestosterone (DHT, 10 mg/kg) and the compound of the present invention (Example 60, 60 mg/kg), each dissolved in a 5% dimethyl sulfoxide-containing olive oil solution, were subcutaneously injected once daily, 5 days weekly, for 4 weeks. On the next day after final administration, the wet weight of the ventral prostate was measured to evaluate the AR agonistic effect of the compound of the present invention. On the next day following final administration, moreover, the right femur was removed, and fixed overnight in a 10% neutrally buffered formalin solution. Then, the bone mineral density at the site ranging from the diaphysis to the proximal end was measured by the method of double energy X-ray absorption using a bone mineral content-measuring machine (Aloka, DCS-600) to evaluate increasing action of bone mineral density of the compound of the present invention. The results are shown in Table 14.

TABLE 14

| | Prostate weight (mg/body weight 100 g) | Bone mineral density (mg/cm$^2$) |
|---|---|---|
| Normal control (Sham) | 104 ± 18 | 132 ± 5 |
| ORX Comp. Ex. (Vehicle) | 9 ± 2$^{++}$ | 124 ± 5$^{++}$ |
| DHT 10 mg/kg | 150 ± 14** | 131 ± 7 |
| Ex. 60 60 mg/kg | 56 ± 13** | 132 ± 7* |

Mean ± SD
*p < 0.05,
**p < 0.01 on Dunnett's t-test (vs Vehicle).
$^{++}$p < 0.01 on unpaired t-test (vs Sham).

The compound of Example 60, when consecutively administered for 4 weeks, showed significant increases in the prostate weights in comparison with the,comparative example, and significantly increased the bone mineral density in comparison with the comparative example. Thus, this compound showed excellent AR agonistic activity.

TEST EXAMPLE 5

Inhibitory Action on Testosterone-induced Prostate Weight Increase in Orchiectomized Rats Testes were removed from 8-week-old male SD rats. From 5 days postoperation, 1 mg/kg of testosterone propionate (hereinafter referred to as TP) and 30 mg/kg of the compound of the present invention were simultaneously injected once daily for one consecutive week. The compound of the present invention was suspended in a 0.5% methyl cellulose solution, while TP was dissolved in cottonseed oil containing 5% ethanol. Each of the test compounds was subcutaneously administered. On the next day after final administration, the wet weight of the ventral prostate was measured to evaluate the AR antagonistic effect of the compound of the present invention on TP-induced prostate weight increase. The results are shown in Table 15.

TABLE 15

| | Prostate weight (mg/body weight 100 g) |
|---|---|
| Comp. Ex. (Veh) | 15.7 ± 18 |
| TP treatment group | 80.4 ± 13.7 |
| Example 9 | 60.5 ± 10.7* |
| Example 19 | 58.2 ± 17.7** |
| Example 40 | 55.9 ± 6.3** |

Mean ± SD
*p < 0.05,
**p < 0.01 on Dunnett's t-test.

The compounds of Examples 9, 19 and 40 significantly inhibited the action of TP and showed an excellent AR antagonistic activity.

Preparation examples of the compound of the present invention will be shown below, but dosage forms of the compound are not restricted to them.

PREPARATION EXAMPLE 1

Tablets

Tablets containing 2 mg of an active ingredient per tablet were prepared using the ingredients below:

| | |
|---|---|
| Compound of Example 1 | 2 mg |
| Starch | 48 mg |
| Lactose | 30 mg |
| Cellulose, microcrystalline | 15 mg |
| Methyl cellulose | 3 mg |
| Magnesium stearate | 2 mg |
| Total amount | 100 mg |

PREPARATION EXAMPLE 2

Capsules

In accordance with the following formulation, 100 mg of an ingredient mixture containing 2 mg of an active ingredient per capsule were encapsulated to prepare capsules:

| | |
|---|---|
| Compound of Example 1 | 2 mg |
| Starch | 38 mg |
| Lactose | 50 mg |
| Cellulose, microcrystalline | 8 mg |
| Magnesium stearate | 2 mg |
| Total | 100 mg |

Industrial Applicability

The tetrahydroquinoline derivatives of the present invention, and pharmaceuticals containing them as active ingredients have a specific and strong binding affinity for AR, and have an AR agonistic or antagonistic action. Thus, they can specifically modulate the function of AR, and can prevent and treat various AR-dependent diseases.

What is claimed is:

1. A tetrahydroquinoline derivative represented by the following formula or salts thereof:

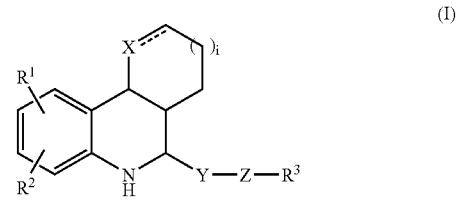

(I)

wherein R$^1$ and R$^2$ each independently represent a hydrogen atom, an alkyl group having 1–9 carbon atoms, an alkoxy group having 1–9 carbon atoms, a nitro group, NR$^4$R$^5$ (wherein R$^4$ and R$^5$ each independently represent a cycloalkyl group having 3–7 carbon atoms, an aralkyl group having 7–9 carbon atoms, an aryl group, an aliphatic acyl group having 2–5 carbon atoms, an aliphatic acyloxy group having 2–5 carbon atoms, an aromatic acyl group, an aliphatic sulfonyl group having 1–4 carbon atoms, an aromatic sulfonyl group, an alkoxycarbonyl group having 2–5 carbon atoms, a hydroxyoxalyl group or an alkoxyoxalyl group having 3–7 carbon atoms), an aliphatic sulfinyl group having 1–4 carbon atoms, an aliphatic sulfonyl group having 1–4 carbon atoms, a cyano group, a sulfamoyl group, an aliphatic sulfamoyl group having 1–4 carbon atoms, an amidino group, a trifluoromethyl group, a trifluoromethoxy group or a tetrafluoroethoxy group, provided that both of R$^1$ and R$^2$ are not a hydrogen atom; X represents CH, CH$_2$, O, or $NR^6$ (wherein $R^6$ independently has the same meaning as $R^4$), provided that when X is CH, the dashed line in the formula signifies a double bond; i represents an integer of 0 when X is CH, $CH_2$ or $NR^6$ and i represents an integer of 0 or 1 when X is O; Y represents an alkylene group having 1–9 carbon atoms that may optionally be substituted by an alkyl group having 1–9 carbon atoms, a cycloalkyl group having 3–7 carbon atoms, a hydroxyl group, an alkoxy group having 1–9 carbon atoms or $NR^7R^8$ (wherein $R^7$ and $R^8$ each independently have the same meaning as $R^4$); Z represents a single bond, —O—, —OCO—, —$OSO_2$—, —S—, —SCO—, —SO—, —$SO_2$—, —$NR^9$—, —$NR^9CO$—, $NR^9SO_2$—, —$NR^9CONH$—, —$NR^9CSNH$—, —$NR^9COO$— or —$NR^9COCO$— (wherein $R^9$ represents a hydrogen atom, an alkyl group having 1–9 carbon atoms, a cycloalkyl group having 3–7 carbon atoms, an aralkyl group having 7–9 carbon atoms, an alkoxyalkyl group having 2–5 carbon atoms or an aryl group that may optionally be substituted by $R^{10}$ (wherein $R^{10}$ is an alkyl group having 1–9 carbon atoms, an alkoxy group having 1–9 carbon atoms, a halogen atom, a nitro group, an aryl group, $NR^{11}R^{12}$ (wherein $R^{11}$ and $R^{12}$ each independently have the same meaning as $R^4$), a carboxyl group, an alkoxycarbonyl group having 2–5 carbon atoms, an amido group, an alkylamido group having 2–5 carbon atoms, an alkylthio group having 1–4 carbon atoms, an aliphatic sulfinyl group having 1–4 carbon atoms, an aliphatic sulfonyl group having 1–4 carbon atoms, a cyano group, a sulfamoyl group, an aliphatic sulfamoyl group having 1–4 carbon atoms, a trifluoromethyl group, a trifluoromethoxy group or a tetrafluoroethoxy group)); $R^3$ represents a hydrogen atom, an alkyl group having 1–9 carbon atoms, a cycloalkyl group having 3–7 carbon atoms, an aralkyl group having 7–9 carbon atoms, an alkoxy group having 1–9 carbon atoms, an alkoxyalkyl group having 2–5 carbon atoms, a halogen atom, a substituted silyl group or an aryl group that may optionally be substituted by $R^{13}$ (wherein $R^{13}$ independently has the same meaning as $R^{10}$), provided that $R^3$ represents a halogen atom only when Z is a single bond.

2. A pharmaceutical composition comprising the tetrahydroquinoline derivative or salts thereof according to claim 1.

* * * * *